United States Patent [19]
Sosa-Pineda et al.

[11] Patent Number: 6,071,697
[45] Date of Patent: Jun. 6, 2000

[54] METHOD FOR TESTING THE DIFFERENTIATION STATUS IN PANCREATIC CELLS OF A MAMMAL

[75] Inventors: Beatriz Sosa-Pineda, Memphis, Tenn.; Peter Gruss, Göttingen, Germany

[73] Assignee: Max-Planck Gesellschaft zur Förderung der Wissenschaften e.V., Berlin, Germany

[21] Appl. No.: 08/778,423

[22] Filed: Dec. 31, 1996

Related U.S. Application Data

[62] Division of application No. 08/778,394, Dec. 31, 1996, which is a continuation of application No. 08/381,841, filed as application No. PCT/EP93/02051, Aug. 2, 1993.

[30] Foreign Application Priority Data

Aug. 3, 1992 [DE] Germany .............................. 42 25 569

[51] Int. Cl.$^7$ ............................ C12Q 1/68; A61K 37/00; A61K 48/00; C07K 13/00
[52] U.S. Cl. ..................................... 435/6; 514/2; 514/44; 530/350
[58] Field of Search .................................. 435/6; 514/44, 514/2; 935/77; 530/350

[56] References Cited

PUBLICATIONS

Paillard. Human Gene Therapy, 8:2009–2010, Nov. 1997.
Correll et al. Human Gene Therapy 1:227–287, 1990.
Orkin et al. Report and Recommendations of the Panel to Assess the NIH Investment in Research on Gene Therapy pp. 1–38, Dec. 1995.
Walther et al. Genomics 11:424–434, Oct. 1991.
Tamura et al. Cytogenet Cell Genet. 66:132–134, Mar. 1994.

*Primary Examiner*—Jeffrey Fredman
*Attorney, Agent, or Firm*—Thomas J. Kowalski; Frommer Lawrence & Haug LLP

[57] ABSTRACT

The present invention relates to a novel method for testing the developmental status in pancreatic cells of a mammal. The present invention further relates to applications in the medical field that directly arise from the method of the invention. Additionally, the present invention relates to transgenic mammals comprising at least one inactivated Pax4 allele and optionally at least one inactivated Pax6 allele.

41 Claims, 37 Drawing Sheets

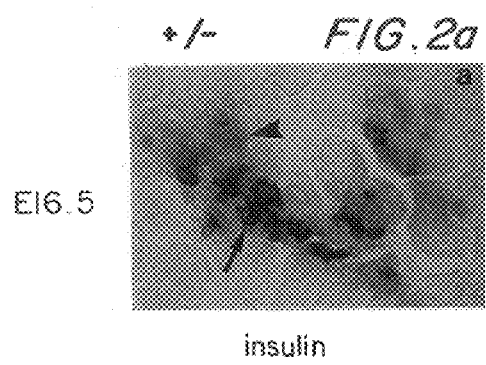
FIG. 2a +/- E16.5 insulin
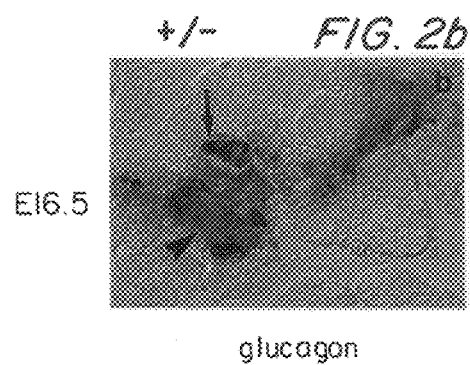
FIG. 2b +/- E16.5 glucagon
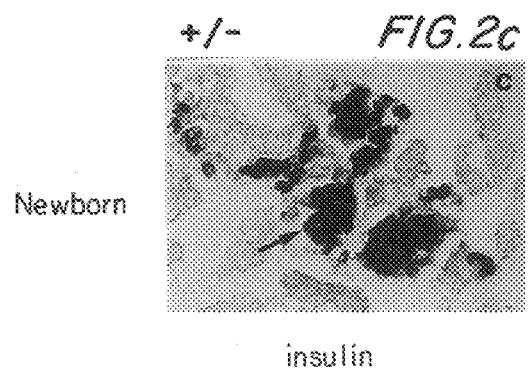
FIG. 2c +/- Newborn insulin
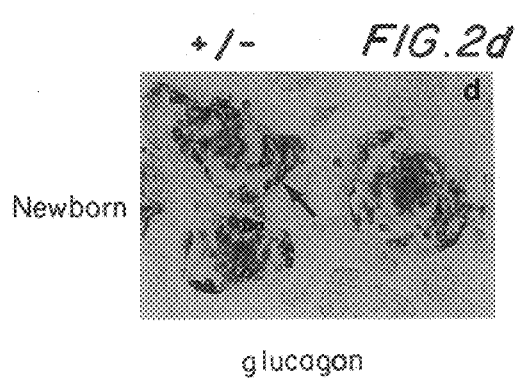
FIG. 2d +/- Newborn glucagon

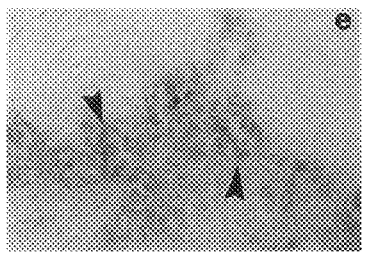
FIG.2e insulin (E16.5, -/-)
FIG.2f glucagon (E16.5, -/-)
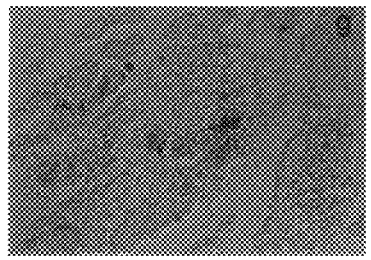
FIG.2g insulin (Newborn, -/-)
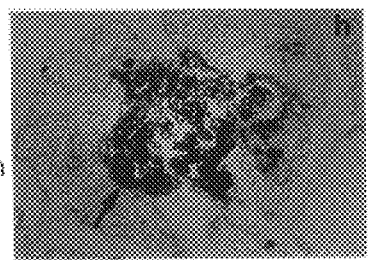
FIG.2h glucagon (Newborn, -/-)

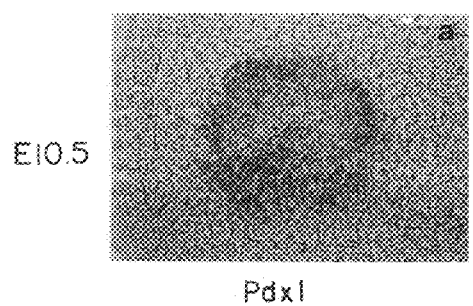 FIG. 3a +/+ E10.5 Pdx1
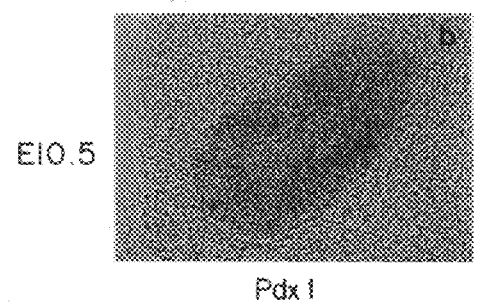 FIG. 3b -/- E10.5 Pdx1
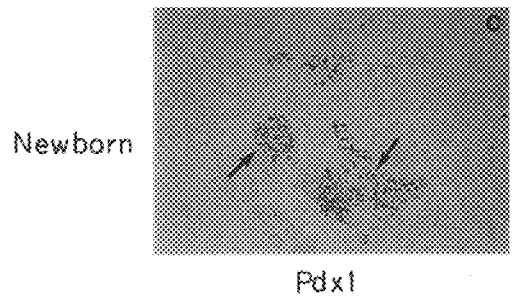 FIG. 3c +/+ Newborn Pdx1
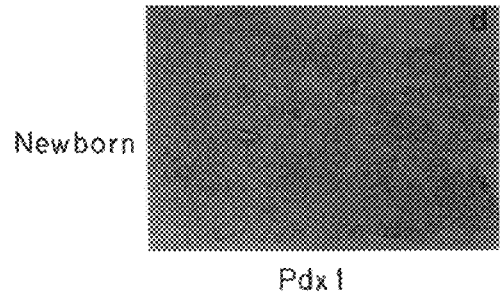 FIG. 3d -/- Newborn Pdx1

Newborn somatostatin

−/−

Newborn somatostatin

| FIG.6a |
|--------|
| FIG.6b |
| FIG.6c |
| FIG.6d |

FIG. 6

(1) GENERAL INFORMATION:

(iii) NUMBER OF SEQUENCES: 16

(2) INFORMATION FOR SEQ ID NO: 1:

(i) SEQUENCE CHARACTERESTICS:

(A) LENGTH: 1275 base pairs (B) TYPE: nucleic acid (C) STRANDEDNESS: single (D) TOPOLOGY: linear (ii) MOLECULE TYPE: other nucleic acid (xi) SEQUENCE DESCRIPTION : SEQ ID NO: 1:

```
ACC AGC AAC CCT GGA GCC TGC ACA GAC CCT GAG ACC TCT TCC TGA ATT CCC ACC    54
TTT TTT CCT CCA TCC AGT ACC AGT CCC AAA GAG AAA CTT CCA GAA GGA GCT CTC CGT TTT   114
CAG TTT GCC AGT TGG CTT CCT GTC CTT CTG CGA GGA GTA CCA GTG TGA AGC ATG CAG CAG   174
                                                                Met Gln Gln
                                                                  1
```

```
GAC GGA CTC AGC AGT GTG AAT CAG CTA GGG GGA CTC TTT GTG AAT GGC CGG CCC CTT CCT    234
Asp Gly Leu Ser Ser Val Asn Gln Leu Gly Gly Leu Phe Val Asn Gly Arg Pro Leu Pro
              5                      10                     15                     20

CTG GAC ACC AGG CAG CAG ATT GTG CAG CTA GCA ATA AGA GGG ATG CGA CCC TGT GAC ATT    294
Leu Asp Thr Arg Gln Gln Ile Val Gln Leu Ala Ile Arg Gly Met Arg Pro Cys Asp Ile
              25                     30                     35                     40

TCA CGG AGC CTT AAG GTA TCT AAT GGC TGT GTG AGC AAG ATC CTA GGA CGC TAC TAC CGC    354
Ser Arg Ser Leu Lys Val Ser Asn Gly Cys Val Ser Lys Ile Leu Gly Arg Tyr Tyr Arg
              45                     50                     55                     60

ACA GGT GTC TTG GAA CCC AAG TGT ATT GGG GGA AGC AAA CCA GCC ACA CCT GCT            414
Thr Gly Val Leu Glu Pro Lys Cys Ile Gly Gly Ser Lys Pro Arg Leu Ala Thr Pro Ala
              65                     70                     75                     80

GTG GTG GCT CGA ATT GCC CAG CTA AAG GAT GAG TAC CCT GCT CTT TTT GCC TGG GAG ATC    474
Val Val Ala Arg Ile Ala Gln Leu Lys Asp Glu Tyr Pro Ala Leu Phe Ala Trp Glu Ile
              85                     90                     95                    100

CAA CAC CAG CTT TGC ACT GAA GGG CTT TGT ACC CAG GAC AAG GCT CCC AGT GTG TCC TCT    534
Gln His Gln Leu Cys Thr Glu Gly Leu Cys Thr Gln Asp Lys Ala Pro Ser Val Ser Ser
             105                    110                    115                    120
```

*FIG. 6b*

```
ATC AAT CGA GTA CTT CGG GCA CTT CAG GAA GAC CAG AGC TTG CAC TGG ACT CAA CTC AGA   594
Ile Asn Arg Val Leu Arg Ala Leu Gln Glu Asp Gln Ser Leu His Trp Thr Gln Leu Arg
125                         130                         135                 140

TCA CCA GCT GTG TTG GCT CCA GTT CTT CCC AGT AAC TGT GGG GCT CCC CGA             654
Ser Pro Ala Val Leu Ala Pro Val Leu Pro Ser Asn Cys Gly Ala Pro Arg
145                         150                         155                 160

GGC CCC CAC CCA GGA ACC AGC CAC AGG AAT CGG GCT ATC TTC TCC CCG GGA CAA GCC GAG   714
Gly Pro His Pro Gly Thr Ser His Arg Asn Arg Ala Ile Phe Ser Pro Gly Gln Ala Glu
165                         170                         175                 180

GCA CTG GAG AAA GAG TTT CAG CGT GGG CAG TAT CCA GAT TCA GTG GCC CGT GGG AAG CTG   774
Ala Leu Glu Lys Glu Phe Gln Arg Gly Gln Tyr Pro Asp Ser Val Ala Arg Gly Lys Leu
185                         190                         195                 200

GCT GCT GCC ACC TCT CTG CCT GAA GAC ACG GTG AGG GTT TGG TTT TCT AAC AGA AGA GCC   834
Ala Ala Ala Thr Ser Leu Pro Glu Asp Thr Val Arg Val Trp Phe Ser Asn Arg Arg Ala
205                         210                         215                 220

AAA TGG CGC AGG CAA GAG CAA AAG CTG AAA TGG GAA GCA CAG CTG CCA GGT GCT TCC CAG GAC   894
Lys Trp Arg Arg Gln Glu Gln Lys Leu Lys Trp Glu Ala Gln Leu Pro Gly Ala Ser Gln Asp
225                         230                         235                 240
```

FIG. 6c

```
CTG ACG ATA CCA AAA AAT TCT CCA GGG ATC ATC TCT GCA CAG CAG TCC CCC GGC AGT GTA    954
Leu Thr Ile Pro Lys Asn Ser Pro Gly Ile Ile Ser Ala Gln Gln Ser Pro Gly Ser Val
245                     250                     255                     260

CCC TCA GCT GCC TTG CCT GTG CTG GAA CCA TTG AGT CCT TCC TTC TGT CAG CTA TGC TGT   1014
Pro Ser Ala Ala Leu Pro Val Leu Glu Pro Leu Ser Pro Ser Phe Cys Gln Leu Cys Cys
265                     270                     275                     280

GGG ACA GCA CCA GGC AGA TGT TCC AGT GAC ACC TCA TCC CAG GCC TAT CTC CAA CCC TAC   1074
Gly Thr Ala Pro Gly Arg Cys Ser Ser Asp Thr Ser Ser Gln Ala Tyr Leu Gln Pro Tyr
285                     290                     295                     300

TGG GAC TGC CAA TCC CTC CTT CCT GTG GCT TCC TCA TAT GTG GAA TTT GCC TGC CCT       1134
Trp Asp Cys Gln Ser Leu Leu Pro Val Ala Ser Ser Tyr Val Glu Phe Ala Cys Pro
305                     310                     315                     320

GCC TCA CCA CCC ATC CTG TGC ATC ATC TGA TTG GAG GCC CAG GAC AAG TGC CAT CAT CCC   1194
Ala Ser Pro Pro Ile Leu Cys Ile Ile
325                     330

ATT GCT CAA ACT GGC CAT AAG ACA CCT CTA TTT GAC AGT AAT AAA AAC CTT TTC TTA GAT   1254
                                                                                  FIG.6d
GTT AAA AAA AAA GGG GGG   1275
```

FIG.7a

| FIG.7a |
|--------|
| FIG.7b |
| FIG.7c |

FIG.7

(2) INFORMATION FOR SEQ ID NO: 2:

(i) SEQUENCE CHARACTERESTICS:

(A) LENGTH: 332 amino acids
        (B) TYPE: amino acid
        (D) TOPOLOGY: linear (ii) MOLECULE TYPE: protein (xi) SEQUENCE DESCRIPTION : SEQ ID NO: 2:

```
                                            Met Gln Gln
                                             1
Asp Gly Leu Ser Ser Val Asn Gln Leu Gly Gly Leu Phe Val Asn Gly Arg Pro Leu Pro
                         5                  10                  15              20
Leu Asp Thr Arg Gln Gln Ile Val Gln Leu Ala Ile Arg Gly Met Arg Pro Cys Asp Ile
            25                  30                  35                  40
Ser Arg Ser Leu Lys Val Ser Asn Gly Cys Val Ser Lys Ile Leu Gly Arg Tyr Tyr Arg
            45                  50                  55                  60
Thr Gly Val Leu Glu Pro Lys Cys Ile Gly Gly Ser Lys Pro Arg Leu Ala Thr Pro Ala
            65                  70                  75                  80
```

Val Val Ala Arg Ile Ala Gln Leu Lys Asp Glu Tyr Pro Ala Leu Phe Ala Trp Glu Ile
  85              90              95             100

Gln His Gln Leu Cys Thr Glu Gly Leu Cys Thr Gln Asp Lys Ala Pro Ser Val Ser Ser
 105             110             115             120

Ile Asn Arg Val Leu Arg Ala Leu Gln Glu Asp Gln Ser Leu His Trp Thr Gln Leu Arg
 125             130             135             140

Ser Pro Ala Val Leu Ala Pro Val Leu Pro Ser Pro His Ser Asn Cys Gly Ala Pro Arg
 145             150             155             160

Gly Pro His Pro Gly Thr Ser His Arg Asn Arg Ala Ile Phe Ser Pro Gly Gln Ala Glu
 165             170             175             180

Ala Leu Glu Lys Glu Phe Gln Arg Gly Gln Tyr Pro Asp Ser Val Ala Arg Gly Lys Leu
 185             190             195             200

Ala Ala Ala Thr Ser Leu Pro Glu Asp Thr Val Arg Val Trp Phe Ser Asn Arg Arg Ala
 205             210             215             220

Lys Trp Arg Arg Gln Glu Lys Leu Lys Trp Glu Ala Gln Leu Pro Gly Ala Ser Gln Asp
 225             230             235             240

Leu Thr Ile Pro Lys Asn Ser Pro Gly Ile Ile Ser Ala Gln Ser Pro Gly Ser Val
 245             250             255             260

FIG. 7b

```
Pro Ser Ala Ala Leu Pro Val Leu Glu Pro Leu Ser Pro Ser Phe Cys Gln Leu Cys Cys
265                 270                 275                 280

Gly Thr Ala Pro Gly Arg Cys Ser Ser Asp Thr Ser Ser Gln Ala Tyr Leu Gln Pro Tyr
285                 290                 295                 300

Trp Asp Cys Gln Ser Leu Leu Pro Val Ala Ser Ser Tyr Val Glu Phe Ala Cys Pro
305                 310                 315                 320

Ala Ser Pro Pro Ile Leu Cys Ile Ile
325                 330
```

| FIG. 8a |
|---|
| FIG. 8b |
| FIG. 8c |
| FIG. 8d |
| FIG. 8e |
| FIG. 8f |

FIG. 8

(2) INFORMATION FOR SEQ ID NO: 3:

(i) SEQUENCE CHARACTERESTICS:

(A) LENGTH: 2481 base pairs (B) TYPE: nucleic acid (C) STRANDEDNESS: single (D) TOPOLOGY: linear (ii) MOLECULE TYPE: other nucleic acid (xi) SEQUENCE DESCRIPTION : SEQ ID NO: 3:

```
ACA ACG ACG AAA GAG AGG ATG CCT CTT AAA GGC AGA AGA CTT TAA CCA AGG GCG    54
GTG AGC AGA TGT GTG AGA TCT TCT ATT CTA GAA GTG GAC GTA TAT CCC AGT TCT CAG AGC   114

CCC GTA TTC GAG CCC CGT GGG ATC CGG AGG CTG CCA ACC AGC TCC AGC ATG CAG AAC AGT   174
                                                                Met Gln Asn Ser
                                                                 1
```

```
CAC AGC GGA GTG AAT CAG CTT GGT GGT GTC TTT GTC AAC GGG CCA CTG CCG GAC TCC    234
His Ser Gly Val Asn Gln Leu Gly Gly Val Phe Val Asn Gly Arg Pro Leu Pro Asp Ser
 5                  10                  15                  20

ACC CGG CAG AAG ATC GTA GAG CTA GCT CAC AGC GGG GCC CGG CCG TGC GAC ATT TCC CGA    294
Thr Arg Gln Lys Ile Val Glu Leu Ala His Ser Gly Ala Arg Pro Cys Asp Ile Ser Arg
      25                  30                  35                  40

ATT CTG CAG ACC CAT GCA GAT GCA AAA GTC CAG GTG CTG GAC AAT GAA AAC GTA TCC AAC    354
Ile Leu Gln Thr His Ala Asp Ala Lys Val Gln Val Leu Asp Asn Glu Asn Val Ser Asn
          45                  50                  55                  60

GGT TGT GTG AGT AAA ATT CTG GGC AGG TAT TAC GAG ACT GGC TCC ATC AGA CCC AGG GCA    414
Gly Cys Val Ser Lys Ile Leu Gly Arg Tyr Tyr Glu Thr Gly Ser Ile Arg Pro Arg Ala
              65                  70                  75                  80

ATC GGA GGG AGT AAG CCA AGA GTG GCG ACT CCA GAA GTT GTA AGC AAA ATA GCC CAG TAT    474
Ile Gly Gly Ser Lys Pro Arg Val Ala Thr Pro Glu Val Val Ser Lys Ile Ala Gln Tyr
                  85                  90                  95                 100

AAA CGG GAG TGC CCT TCC ATC TTT GCT TGG GAA ATC CGA GAC AGA TTA TTA TCC GAG GGG    534
Lys Arg Glu Cys Pro Ser Ile Phe Ala Trp Glu Ile Arg Asp Arg Leu Leu Ser Glu Gly
                     105                 110                 115                 120
```

FIG. 8b

```
GTC TGT ACC AAC GAT AAC ATA CCC AGT GTG TCA TCA ATA AAC AGA GTT CTT CGC AAC CTG      594
Val Cys Thr Asn Asp Asn Ile Pro Ser Val Ser Ser Ile Asn Arg Val Leu Arg Asn Leu
125                     130                 135                 140

GCT AGC GAA AAG CAA CAG ATG GGC GCA GAC GGC ATG TAT GAT AAA CTA AGG ATG TTG AAC      654
Ala Ser Glu Lys Gln Gln Met Gly Ala Asp Gly Met Tyr Asp Lys Leu Arg Met Leu Asn
145                     150                 155                 160

GGG CAG ACC GGA AGC TGG GGC ACA CGC CCT GGT TGG TAT TAT CCC GGG ACT TCA GTA CCA GGG  714
Gly Gln Thr Gly Ser Trp Gly Thr Arg Pro Gly Trp Tyr Tyr Pro Gly Thr Ser Val Pro Gly
165                     170                 175                 180

CAA CCC ACG CAA GAT GGC TGC CAG CAA CAG GAA GGA GGG GGA GAG AAC ACC AAC TCC ATC      774
Gln Pro Thr Gln Asp Gly Cys Gln Gln Gln Glu Gly Gly Gly Glu Asn Thr Asn Ser Ile
185                     190                 195                 200

AGT TCT AAC GGA GAA GAC TCG GAT GAA GCT CAG ATG CGA CTT CAG CTG AAG CGG AAG CTG      834
Ser Ser Asn Gly Glu Asp Ser Asp Glu Ala Gln Met Arg Leu Gln Leu Lys Arg Lys Leu
205                     210                 215                 220

CAA AGA AAT AGA ACA TCT TTT ACC CAA GAG CAG ATT GAG CAG GCT CTG GAG AAA GAG TTT GAG  894
Gln Arg Asn Arg Thr Ser Phe Thr Gln Glu Gln Ile Glu Gln Ala Leu Glu Lys Glu Phe Glu
225                     230                 235                 240
```

FIG. 8c

```
AGG ACC CAT TAT CCA GAT GTG TTT GCC CGG GAA AGA CTA GCA GCC AAA ATA GAT CTA CCT   954
Arg Thr His Tyr Pro Asp Val Phe Ala Arg Glu Arg Leu Ala Ala Lys Ile Asp Leu Pro
245                 250                 255                 260

GAA GCA AGA ATA CAG GTA TGG TTT TCT AAT CGA AGG GCC AAA TGG AGA AGA GAA GAG AAA  1014
Glu Ala Arg Ile Gln Val Trp Phe Ser Asn Arg Arg Ala Lys Trp Arg Arg Glu Glu Lys
265                 270                 275                 280

CTG AGG AAC CAG AGA AGA CAG GCC AGC AAC ACT CCT AGT CAC ATT CCT ATC AGC AGC AGC  1074
Leu Arg Asn Gln Arg Arg Gln Ala Ser Asn Thr Pro Ser His Ile Pro Ile Ser Ser Ser
285                 290                 295                 300

TTC AGT ACC AGT GTC TAC CAG ATC CCA CAG CCC ACC ACA CCT GTC TCC TTC ACA          1134
Phe Ser Thr Ser Val Tyr Gln Ile Pro Gln Pro Thr Thr Pro Val Ser Ser Phe Thr
305                 310                 315                 320

TCA GGT TCC ATG TTG GGC CGA ACA GAC ACC GCC CTC ACC AAC ACG TAC AGT GCT TTG CCA  1194
Ser Gly Ser Met Leu Gly Arg Thr Asp Thr Ala Leu Thr Asn Thr Tyr Ser Ala Leu Pro
325                 330                 335                 340

CCC ATG CCC AGC TTC ACC ATG GCA AAC AAC CTG CCT ATG CAA CCC CCA GTC CCC AGT CAG  1254
Pro Met Pro Ser Phe Thr Met Ala Asn Asn Leu Pro Met Gln Pro Pro Val Pro Ser Gln
345                 350                 355                 360
```

*FIG. 8d*

```
ACC TCC TCA TAC TCG TGC ATG CTG CCC ACC AGC CCG TCA GTG AAT GGG CGG AGT TAT GAT   1314
Thr Ser Ser Tyr Ser Cys Met Leu Pro Thr Ser Pro Ser Val Asn Gly Arg Ser Tyr Asp
365                 370                 375                 380

ACC TAC ACC CCT CCG CAC ATG CAA ACA CAC ATG AAC AGT CAG CCC ATG GGC ACC TCG GGG   1374
Thr Tyr Thr Pro Pro His Met Gln Thr His Met Asn Ser Gln Pro Met Gly Thr Ser Gly
385                 390                 395                 400

ACC ACT TCA ACA GGA CTC ATT TCA CCT GGA GTG TCA CCT GTC CAA GTT CCC GGG AGT   1434
Thr Thr Ser Thr Gly Leu Ile Ser Pro Gly Val Ser Val Pro Val Gln Val Pro Gly Ser
405                 410                 415                 420

GAA CCT GAC ATG TCT CAG TAC TGG CCT CGA TTA CAG TAA AGA GAG AAG GAG AGA GCA TGT   1494
Glu Pro Asp Met Ser Gln Tyr Trp Pro Arg Leu Gln
425                 430                 435

GAT CGA GAG AGG AAA TTG TGT TCA CTC TGC CAA TGA CTA TGT GGA CAC AGC AGT TGG GTA   1554

TTC AGG AAA GAA AGA GAA ATG GCG GTT AGA AGC ACT TCA CTT TGT AAC TGT CCT GAA CTG   1614

GAG CCC GGG AAT GGA CTA GAA CCA AGG ACC TTG CGT ACA GAA GGC ACG GTA TCA GTT GGA   1674

ACA AAT CTT CAT TTT GGT ATC CAA ACT TTT ATT CAT TTT GGT GTA TTA TTT GTA AAT GGG   1734
```

FIG. 8e

```
CAT TGG TAT GTT ATA ATG AAG AAA AGA ACA ACA CAG GCT GTT GGA TCG CGG ATC TGT GTT  1794
GCT CAT GTG GTT GTT TAA AGG AAA CCA TGA TCG ACA AGA TTT GCC ATG GAT TTA AGA GTT  1854
TTA TCA AGA TAT ATC AAA TAC TTC TCC CCA TCT GTT CAT AGT TTA TGG ACT GAT GTT CCA  1914
AGT TTG TAT TCC TTT GCA TAT AAT TGA ACC TGG GAC AAC ACA CAC TAG ATA TAT GTA      1974
AAA ACT ATC TGT TGG TTT TCC AAA GGT TGT TAA CAG ATG AAG TTT ATG TGC AAA AAA GGG  2034
TAA GAT ATG AAT TCA AGG AGA AGT TGA TAG CTA AAA TGT AAG TAT TTG TCT TCC CTA      2094
ACA ATT TGT TTT ATG TCA AAA TGT AAG TAT TTG TCT TCC CTA GAA ATC CTC AGA ATG ATT  2154
TCT ATA ATA AAG TTA ATT TCA TTT ATA TTT GAC AAG AAT ACT CTA TAG ATG TTT TAT ACA  2214
CAT TTT CAT GCA ATC ATT TGT TTC TTT CTT GGC CAG CAA AAG TTA ATT GTT CTT AGA TAT  2274
AGC TGT ATT ACT GTT CAC AGT CCA ATC ATT TTG TGC ATC TAG AAT TCA TTC CTA ATC AAT  2334
TAA AAG TGC TTG CAA GAG TTT TAA GTG TTT TGC AGT TGT TCA CAA ATA CAT ATC          2394
AAA ATT AAC CAT TGT TGA TTG TAA AAA AAC CAT GCC AAA GCC TTT GTA TTT TCT TTA      2454
TTA CCC TTG ACC GTA AGA CAT GAA TTC  2481
```

| FIG.9a |
|--------|
| FIG.9b |
| FIG.9c |

FIG. 9

(2) INFORMATION FOR SEQ ID NO: 4:

(i) SEQUENCE CHARACTERESTICS:

(A) LENGTH: 436 amino acids
      (B) TYPE: amino acid
      (D) TOPOLOGY: linear (ii) MOLECULE TYPE: protein (xi) SEQUENCE DESCRIPTION : SEQ ID NO: 4:

```
Met Gln Asn Ser His Ser Gly Val Asn Gln Leu Gly Gly Val Phe Val Asn Gly Arg Pro Leu Pro Asp Ser
 1               5                  10                  15                  20
Thr Arg Gln Lys Ile Val Glu Leu Ala His Ser Gly Ala Arg Pro Cys Asp Ile Ser Arg
                25                  30                  35                  40
Ile Leu Gln Thr His Ala Asp Ala Lys Val Gln Val Leu Asp Asn Glu Asn Val Ser Asn
                45                  50                  55                  60
Gly Cys Val Ser Lys Ile Leu Gly Arg Tyr Tyr Glu Thr Gly Ser Ile Arg Pro Arg Ala
                65                  70                  75                  80
```

FIG. 9b

```
Ile Gly Gly Ser Lys Pro Arg Val Ala Thr Pro Glu Val Val Ser Lys Ile Ala Gln Tyr
 85              90              95             100
Lys Arg Glu Cys Pro Ser Ile Phe Ala Trp Glu Ile Arg Asp Arg Leu Ser Glu Gly
105             110             115            120
Val Cys Thr Asn Asp Asn Ile Pro Ser Val Ser Ser Ile Asn Arg Val Leu Arg Asn Leu
125             130             135            140
Ala Ser Glu Lys Gln Met Gly Ala Asp Gly Met Tyr Asp Lys Leu Arg Met Leu Asn
145             150             155            160
Gly Gln Thr Gly Ser Trp Gly Thr Arg Pro Gly Trp Tyr Pro Gly Thr Ser Val Pro Gly
165             170             175            180
Gln Pro Thr Gln Asp Gly Cys Gln Gln Gln Gly Gly Glu Asn Thr Asn Ser Ile
185             190             195            200
Ser Ser Asn Gly Glu Asp Ser Asp Glu Ala Gln Met Arg Leu Gln Leu Lys Arg Lys Leu
205             210             215            220
Gln Arg Asn Arg Thr Ser Phe Thr Gln Glu Gln Ile Glu Ala Leu Glu Lys Glu Phe Glu
225             230             235            240
Arg Thr His Tyr Pro Asp Val Phe Ala Arg Glu Arg Leu Ala Ala Lys Ile Asp Leu Pro
245             250             255            260
```

```
Glu Ala Arg Ile Gln Val Trp Phe Ser Asn Arg Arg Ala Lys Trp Arg Arg Glu Glu Lys
265                 270                 275                 280

Leu Arg Asn Gln Arg Arg Gln Ala Ser Asn Thr Pro Ser His Ile Pro Ile Ser Ser Ser
285                 290                 295                 300

Phe Ser Thr Ser Val Tyr Gln Pro Ile Pro Gln Pro Thr Thr Pro Val Ser Ser Phe Thr
305                 310                 315                 320

Ser Gly Ser Met Leu Gly Arg Thr Asp Thr Leu Thr Asn Thr Tyr Ser Ala Leu Pro Pro
325                 330                 335                 340

Pro Met Pro Ser Phe Thr Met Ala Asn Asn Leu Pro Met Gln Pro Pro Val Pro Ser Gln
345                 350                 355                 360

Thr Ser Ser Tyr Ser Cys Met Leu Pro Thr Ser Pro Ser Val Asn Gly Arg Ser Tyr Asp
365                 370                 375                 380

Thr Tyr Thr Pro Pro His Met Gln Thr His Met Asn Ser Gln Pro Met Gly Thr Ser Gly
385                 390                 395                 400

Thr Ser Thr Gly Leu Ile Ser Pro Gly Val Ser Val Pro Val Gln Val Pro Gly Ser
405                 410                 415                 420

Glu Pro Asp Met Ser Gln Tyr Trp Pro Arg Leu Gln
425                 430                 435
```

(2) INFORMATION FOR SEQ ID NO: 5:

(i) SEQUENCE CHARACTERESTICS:

(A) LENGTH: 21 base pairs
(B) TYPE: nucleic acid
(C) STRANDEDNESS: single
(D) TOPOLOGY: linear (ii) MOLECULE TYPE: other nucleic acid (xi) SEQUENCE DESRIPTION : SEQ ID NO: 5:

AGCAATAAGA GGGATGCGAC C     21

FIG. 11

(2) INFORMATION FOR SEQ ID NO: 6:

(i) SEQUENCE CHARACTERESTICS:

(A) LENGTH: 21 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION : SEQ ID NO: 6:

AGCTGTGCTT CCCATTTCAG C  21

FIG. 12

(2) INFORMATION FOR SEQ ID NO: 7:

(i) SEQUENCE CHARACTERESTICS:

(A) LENGTH: 33 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION : SEQ ID NO: 7:

GCGAATTCCCC TGAAGTGCCCC GAAGTACTCG ATT 33

FIG.13

(2) INFORMATION FOR SEQ ID NO: 8:

(i) SEQUENCE CHARACTERESTICS:

(A) LENGTH: 20 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION : SEQ ID NO: 8:

GGCTCCGTGA AATGTCACAG   20

FIG.14

(2) INFORMATION FOR SEQ ID NO: 9:

(i) SEQUENCE CHARACTERESTICS:

(A) LENGTH: 30 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION : SEQ ID NO: 9:

CGTAGTACTG TCGACTAGCA GGGIIGGGII GGGIIG    30

FIG. 15

(2) INFORMATION FOR SEQ ID NO: 10:

(i) SEQUENCE CHARACTERESTICS:

(A) LENGTH: 20 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION : SEQ ID NO: 10:

CGTAGTACTG TCGACTAGCA    20

FIG. 16

(2) INFORMATION FOR SEQ ID NO: 11:

(i) SEQUENCE CHARACTERESTICS:

(A) LENGTH: 27 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION : SEQ ID NO: 11:

AACTGGAAGA ATTCGCGGCC GCAGGAA    27

FIG.17

(2) INFORMATION FOR SEQ ID NO: 12:

(i) SEQUENCE CHARACTERESTICS:

(A) LENGTH: 24 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION : SEQ ID NO: 12:

CAGGAAGACC AGAGCTTGCA CTGG    24

FIG. 18

(2) INFORMATION FOR SEQ ID NO: 13:

(i) SEQUENCE CHARACTERESTICS:

(A) LENGTH: 29 base pairs
  (B) TYPE: nucleic acid
  (C) STRANDEDNESS: single
  (D) TOPOLOGY: linear (ii) MOLECULE TYPE: other nucleic acid (xi) SEQUENCE DESCRIPTION : SEQ ID NO: 13:

GCGGATCCCCA CAGGAATCGG GCTATCTTC    29

FIG. 19

(2) INFORMATION FOR SEQ ID NO: 14:

(i) SEQUENCE CHARACTERESTICS:

(A) LENGTH: 20 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION : SEQ ID NO: 14:

GCGCAGGCAA GAGAAGCTGA          20

FIG. 20

(2) INFORMATION FOR SEQ ID NO: 15:

(i) SEQUENCE CHARACTERESTICS:

(A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION : SEQ ID NO: 15:

CTTCCAGAAG GAGCTCTC   18

FIG. 21

(2) INFORMATION FOR SEQ ID NO: 16:

(i) SEQUENCE CHARACTERESTICS:

(A) LENGTH: 19 base pairs
(B) TYPE: nucleic acid
(C) STRANDEDNESS: single
(D) TOPOLOGY: linear (ii) MOLECULE TYPE: other nucleic acid (xi) SEQUENCE DESRIPTION : SEQ ID NO: 16:

TGGGATGATG GCACTTGTC    19

METHOD FOR TESTING THE DIFFERENTIATION STATUS IN PANCREATIC CELLS OF A MAMMAL

RELATED APPLICATIONS

This application is a division of application Ser. No. 08/778,394 filed on Dec. 31. 1996, which is a continuation-in-part of U.S. application Ser. No. 08/381,841, filed Mar. 27, 1995 now U.S. Pat. No. 5,747,250, as the National Phase of PCT/EP93/02051, filed Aug. 2, 1993, designating the U.S. and claiming priority from German application P 42 25 569.4, filed Aug. 3, 1992. Each of the aforementioned U.S., PCT, and German applications are hereby incorporated herein by reference.

FIELD OF THE INVENTION

The present invention relates to methods for testing the differentiation status of pancreatic cells in a mammal; for instance, by ascertaining the level or status of Pax4 mRNA and/or protein in pancreatic cells (or pre-pancreatic cells) and comparing the level or status with the corresponding level or status in normal pancreatic (or pre-pancreatic) cells. This method provides a means for diagnosis or detection of diseases which arise from certain pancreatic cells, especially a means for diagnosis or detection of, for instance, diabetes, such as juvenile diabetes. The method can be performed in conjunction with ascertaining the level or status of Pax6 mRNA and/or protein in pancreatic cells (or pre-pancreatic cells) and comparing the level or status with the corresponding level or status in normal pancreatic (or pre-pancreatic) cells.

The data set forth below shows that deficiency in Pax4 expression is indicative of deficiency or failure in β-cell development and ergo insulin production (and thus diabetes such as juvenile diabetes). The invention thus relates to restoring Pax4 expression for treatment, prevention or delaying a pancreatic disease such as diabetes, e.g., juvenile diabetes; and ergo transgenic mammals having restored Pax4 expression by modification so as to comprise at least one first nucleic acid molecule having a sequence encoding a functional and expressible Pax4 protein and optionally a second nucleic acid sequence encoding a functional and expressible Pax6 protein. Alternatively or additionally, the invention relates to administration of Pax4 alone or with Pax6 and/or of an agent for stimulating expression of Pax4 or Pax4 and Pax6, for treatment, prevention or delaying a pancreatic disease such as diabetes, e.g., juvenile diabetes.

Since the data set forth below shows that deficiency in Pax4 expression is indicative of deficiency or failure in β-cell development, and ergo insulin production (and thus diabetes such as juvenile diabetes), the present invention also relates to transgenic mammals modified so as to comprise at least one inactivated Pax4 allele. This mammal has numerous utilities, including as a research model for pancreatic diseases such as juvenile diabetes; and therefore, presents a novel and valuable animal in the development of therapies, treatment, etc. for diseases caused by deficiency or failure of pancreatic cells. Accordingly, in this instance, the mammal is preferably non-human, e.g., a laboratory animal such as a mouse or rat.

Further, since improper expression of Pax4 may also cause maladies such as tumors, the invention also relates to a transgenic mammal modified so as to comprise at least one inactivated Pax4 allele for treatment, prevention or the delay of a pancreatic disease caused by improper expression of Pax4, such as tumors. In this instance, the mammal can be a human, as the introduction into the mammal of the at least one inactivated Pax4 allele is for therapy. Alternatively or additionally, the invention relates to administration of an agent which inhibits Pax4 or Pax4 and Pax6 for treatment, prevention or delaying a pancreatic disease caused by improper expression of Pax4, such as tumors.

Several documents are cited throughout the text of this specification. Each of the documents cited herein (including manufacturer's specifications, instructions, etc.) are hereby incorporated herein by reference.

BACKGROUND OF THE INVENTION

The pancreas is an essential organ possessing both an exocrine function involved in the delivery of enzymes into the digestive tract and an endocrine function by which various hormones are secreted into the blood stream. The exocrine function is assured by acinar and centroacinar cells that produce various digestive enzymes (amylase, proteases, nuclease, etc.) and intercalated duct cells that transport these enzymes in alkaline solution to the duodenum.

The functional unit of the endocrine pancreas is the islet of Langerhans which are scattered throughout the exocrine portion of the pancreas and are composed of four cell types: α-, β-, δ- and PP-cells, reviewed in Slack, Development 121 (1995), 1569–1580. β-cells produce insulin, represent the majority of the endocrine cells and form the core of the islets, while α-cells secrete glucagon and are located in the periphery. δ-cells and PP-cells are less numerous and respectively secrete somatostatin and a pancreatic polypeptide. Insulin and glucagon are key regulators of blood glucose levels. Insulin lowers blood glucose level by increasing the cellular uptake of glucose and its conversion to glycogen. Glucagon elevates blood glucose levels by intervening with the breakdown of liver glycogen. Common pancreatic disorders affecting endocrine function include diabetes mellitus and hormone secreting tumors.

All four endocrine cells are thought to originate from a common pluripotent precursor that is derived from the endoderm. Early during pancreatic development, these precursors co-express several hormones such as insulin and glucagon. In mouse, the α-cells are the first endocrine cells to differentiate at day 9.5 post-conception (p.c.), followed by the β- and δ-cells at day 14.5 p.c. and the PP-cells at postnatal day 1. Very little is known on the molecular and genetic factors involved in defining the lineage of the different endocrine cells. One of the few genes described so far is the homeobox gene Pdx1 which is expressed during the initial stages of pancreatic development and becomes restricted to the β-cells in adult islets (Guz et al., Development 121 (1995), 11–18). Homozygous mouse Pdx1 mutants fail to develop a pancreas and die a few days after birth (Jonsson et al., Nature 371 (1994), 606–609). Two members of the Pax gene family, Pax4 and Pax6, are also expressed in endocrine cells during pancreatic development. Until now, however, it was not known how in particular the Pax4 and the Pax6 gene affects pancreatic development.

A method for testing for a variety of differentiation parameters in the pancreas was hitherto not available but is nevertheless highly desirable. Results obtainable by such a method have a significant impact on, e.g., the diagnosis and therapy of pancreas related diseases.

SUMMARY OF THE INVENTION

The present invention relates to a novel method for testing the differentiation status of pancreatic cells in mammals. The present invention further relates to applications in the medical field that directly arise from the method of the invention. Additionally, the present invention relates to transgenic mammals comprising at least one inactivated Pax4 gene and optionally at least one inactivated Pax6 gene.

DETAILED DESCRIPTION OF THE INVENTION

Accordingly, a technical problem underlying the present invention was to provide such a method for monitoring the differentiation status of pancreatic cells. The solution to said technical problem is achieved by the embodiments characterized in the claims.

Thus, the present invention relates to a method for testing the differentiation status in pancreatic cells of a mammal comprising (a) determining the level or status of Pax4 mRNA in pancreatic cells of said mammal; and/or (b) determining the level or status of Pax4 protein in pancreatic cells of said mammal; and (c) comparing said level or status of Pax4 mRNA and/or Pax4 protein with the corresponding level in normal pancreatic cells.

In connection with the present invention, the term "level" denotes the amount of mRNA or protein produced. The term "status" includes the options that the gene, mRNA, protein or a transcription control element, e.g. promoter/enhancer sequence may bear a mutation, deletion or any other modifications which would affect the overall activity of the gene when compared to the wild-type normal gene product. Included in this term are post-translational modifications of the protein.

The method of the present invention allows for the first time a detailed study of the development of different cell types, i.e. $\alpha$-, $\beta$-, $\delta$- and PP-cells in the pancreatic tissue. As is demonstrated by the appended examples, the Pax4 gene, optionally in conjunction with the Pax6 gene is involved in the early steps of pancreatic development. This surprising result allows the monitoring of cell fate as well as the investigation of the development of diseases which arise from certain cell types contained in the pancreas. The results presented in accordance with the present invention furthermore allow the conclusion that Pax4 and/or Pax6 are master regulators for specific pancreatic cells. Thus, Pax4 appears to be a master regulator of $\beta$-cells. Pax4 is also expressed in non-pancreatic cells. Pax4 expression is detected in a subset of cells found in the developing spinal cord. Therefore, Pax4 may likewise play a role in the differentiation status of these cells.

Accordingly, the method of the present invention provides a means for diagnosis or detection of diseases which arise from certain pancreatic cells, especially a means for early detection or diagnosis; for instance, detection or diagnosis of diabetes, such as juvenile diabetes; and, such detection or diagnosis can be pre- or post-natal.

In a preferred embodiment, the method of the present invention further comprises (d) determining the level or status of Pax6 mRNA in pancreatic cells of said mammal; and/or (e) determining the level or status of Pax6 protein in pancreatic cells of said mammal; and (f) comparing said level or status of Pax6 mRNA and/or Pax6 protein with the corresponding level in normal pancreatic cells.

This embodiment of the present invention allows the study of the synergistic effects of the Pax4 and the Pax6 gene products. It is expected that the analysis of said synergistic effect provides deeper insights into the regulation of cell specific development in the pancreas. From said deeper insight the development of diagnostic and pharmaceutical compositions related to pancreas-specific diseases will greatly benefit.

In a further preferred embodiment of the method of the invention, said mammal is in the (i) embryonic;

(ii) newborn; or (iii) adult stage.

As has been shown in accordance with the present invention, the Pax4 gene, preferably in conjunction with the Pax6 gene, is expressed at a different level and at different stages of mammalian pancreas development. The specific analysis of the developmental stage of pancreatic cells at the embryonic, newborn or adult stage will provide further insights into, e.g., specific disease states associated with the respective stages. For example, it is expected that the etiology of, e.g., juvenile diabetes will be elucidated by applying the method of the present invention, as well as by employing the transgenic mammals (non-human) according to the invention (discussed infra; see also the examples). Upon the basis of this knowledge, new pharmaceutical active drugs, e.g. against juvenile diabetes, will be developed and tested.

The method of the invention can be applied to a variety of mammals, depending on the purpose of the investigation. Thus, in a preferred embodiment, the mammal is a mouse. This embodiment is particularly useful for basic research to understand more clearly the functional interrelationship of different proteins which regulate the development of the pancreas. In a further embodiment the mammal is a human. In this embodiment, preferably diagnostic and therapeutic applications are envisaged.

In a further preferred embodiment of the method of the invention, steps (a) and optionally (d) and/or (b) and optionally (e) are carried out in vivo.

This embodiment of the invention is expected to be useful in particular in basic research or in therapeutic applications.

In a further preferred embodiment of the method of the invention, steps (a) and optionally (d) and/or (b) and optionally (e) are carried out in vitro.

The advantages of this embodiment would be expected to lie primarily in diagnostic applications and, again, in basic research.

In a further preferred embodiment of the method of the invention, said determination in step (a) and optionally in step (d) is effected by employing (i) a nucleic acid sequence corresponding to at least a part of the Pax4 gene and preferably encoding at least part of the Pax4 protein and optionally a second nucleic acid sequence corresponding to at least a part of the Pax6 gene and preferably encoding at least part of the Pax6 protein;

(ii) a nucleic acid sequence complementary to the nucleic acid sequence(s) of (i); or (iii) a primer or a primer pair hybridizing to the nucleic acid sequence(s) of (i) or (ii).

In accordance with this embodiment of the present invention, the method of testing the differentiation status can be effected by using a nucleic acid molecule encoding the Pax4 gene and/or the Pax6 gene or a part thereof, e.g., in the form of a Southern or Northern blot or in situ analysis. Said nucleic acid sequence may hybridize to a coding region of either of the genes or to a non-coding region. In the case that a complementary sequence in accordance with (ii) is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above-mentioned Pax genes or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of Pax4 and optionally Pax6 can be monitored by using a primer pair that specifically hybridizes to either of the corresponding nucleic acid sequences and by carrying out a PCR reaction according to standard procedures.

Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985.

Further modifications of the above-mentioned embodiment of the invention can be easily devised by the person skilled in the art, without any undue experimentation from this disclosure.

An additional embodiment of the present invention relates to a method wherein said determination in step (b) and optionally of step (e) is effected by employing an antibody or fragment thereof that specifically binds to the Pax4 protein and optionally by employing a second antibody or fragment thereof which specifically binds to the Pax6 protein.

Antibodies or fragments thereof to the aforementioned protein can be obtained by using conventional methods which are described, e.g., in Harlow and Lane "Antibodies, A Laboratory Manual", CSH Press, Cold Spring Harbor, 1988. These antibodies may be monoclonal antibodies or comprised in polyclonal antisera or fragments thereof. The antibody used in the method of the invention may be labeled with detectable tags such as a histidine flags or a biotin molecule.

In a further preferred embodiment of the method of the present invention, said pancreatic cells are β-cells or δ-cells.

In accordance with the present invention, it was found that Pax4 is expressed in β-cells. Disruption of the Pax4 gene function therefore allows a close monitoring of the development of said cells in the pancreas. Since Pax6 is also expressed in both α- and β-cells (see concurrently filed application Ser. No. 08/778,394 (attorney docket 674503-2002, incorporated herein by reference), Pax6 expression may be required to establish a competent background for Pax4 to act.

Since both Pax4 and Pax6 are regulatory proteins required for proper differentiation of endocrine cells, this embodiment may allow a variety of conclusions with regard to the generation of diseases such as pancreatic tumors.

Accordingly, a further preferred embodiment relates to a method wherein said differentiation status is indicative of a malignancy or malignant potential of said pancreatic cell. Overexpression or absence of a functional Pax4 and optionally Pax6 product may induce normal endocrine cells to become cancerous. In accordance with this statement, allelic deletions in chromosome 7 q in the vicinity of the Pax4 gene are observed in many pancreatic carcinomas (Alberto et al., Cancer Res. 56 (1996), 3808–3818). Pax4, and optionally Pax6, may also interact with other oncogenic factors.

Malignancy or malignant potential is used in accordance with this invention preferably but not exclusively in connection with pancreatic tumors such as insulinoma, glucagonomas, somatostatinomas and ductal cell adenocarcinomas.

The present invention relates in a further preferred embodiment to a method that further comprises (a') prior to said testing removal of a solid pancreatic tumor from said mammal; and (b') after said testing, at least partial elimination of the expression of the Pax4 and optionally the Pax6 gene in cells of said tumor, if said gene(s) is/are over-expressed or stimulation of expression of the Pax4 gene and optionally the Pax6 gene or introduction of a functional and expressible Pax4 gene and optionally a functional and expressible Pax6 gene into said cells if said gene(s) is/are under-expressed or not expressed; and (b") reintroducing the cells obtained as a product of step (b') into said mammal.

In this context and as used throughout this specification, "functional" Pax4 (Pax6) means a protein having part or all of the primary structural conformation of the Pax4 (Pax6) protein possessing the biological property of contributing to the development of endocrine cells into β-cells (α-cells and Langerhans cells), said protein being the product of procaryotic or eukaryotic expression of a Pax4 (Pax6) encoding DNA sequence and having an amino acid sequence comprising the amino acid sequence of SEQ ID No. 2 (SEQ ID No. 4) or any fragment or derivative thereof by way of amino acid deletion, substitution, insertion, addition and/or replacement of the amino acid sequence given in SEQ ID No. 2 (SEQ ID No. 4). Also comprised by the term "functional" Pax4 (Pax6) protein is the capability of said protein or part thereof to generate a specific immune response such as an antibody response.

This embodiment of the present invention is suited for therapy of tumors, in particular in humans. Therefore, it is envisaged that pancreatic tumor cells are monitored for the expression level of the Pax4 protein and optionally Pax6 protein. Detection of an over-expression of said protein(s) would allow the conclusion that said over-expression is interrelated to the generation or maintenance of the tumor. Accordingly, a step would be applied to reduce the expression level to normal levels. This can be done, for example, by at least partial elimination of the expression of the Pax4 gene by biological means, for example, by the use of ribozymes, antisense nucleic acid molecules or intracellular antibodies against either the Pax4 or Pax6 protein. Furthermore, pharmaceutical products may be developed that reduce the expression levels of Pax4. While it is presently unclear how Pax4 and optionally Pax6 are regulated in pancreatic tissue, it is possible that different developmental and hormonal factors determine the levels of activity of these genes. For example, small molecules are known to repress the expression of certain genes. It has been demonstrated that activin A, a member of the TGFβ superfamily, can downregulate Pax6 expression in the developing spinal cord (Pituello et al., Proc. Natl. Acad. Sci. USA 92 (1995), 6952–6956). Similar molecules may downregulate Pax4 or optionally Pax6 expression in the pancreas. On the other hand, lack of expression or under-expression may be remedied by a functional Pax4 gene and optionally a functional Pax6 gene which should both be expressible in the tumor cells. Stimulation or induction of expression can be obtained again by the use of small molecules or other means, this time activating Pax4 gene expression. In this regard, it is important to note that the present invention envisages the possibilities that one of said Pax genes is over-expressed whereas the second Pax gene is under-expressed in said malignant state. Finally, surgical removal or chemotherapeutic treatment of pancreatic tumors in humans often leaves the patient without a significant number of insulin producing cells. Pax4 and optionally Pax6 may be used in tissue engineering (Langer and Vacanti, Science 260 (1993), 920–924) for the development of functional substitute for missing or damaged β-cells. Pancreatic tumor cells that have reverted in vitro to a normal levels of Pax4 expression, and optionally of Pax6 expression, can be re-introduced into the patient so that the said patient is provided with normal insulin producing cells of his own genetic background thereby reducing the risk of immunological rejection of the cells.

In a further preferred embodiment of the present invention, the testing for differentiation status in pancreatic cells is a testing for the developmental status in β-cells, which as shown by the examples, is indicative of juvenile diabetes. Juvenile diabetes is often the result of deficiency or failure in β-cell development. The examples show that deficiency in Pax4-expression is indicative of deficiency or failure in β-cell development and ergo insulin production (and thus diabetes such as juvenile diabetes).

Early diagnosis of juvenile diabetes is particularly advantageous and of considerable medical importance. Thus, it is a preferred embodiment to employ methods of the invention for diagnosis or detection of diabetes. This preferred embodiment can be used to diagnose juvenile diabetes in the coronar villi, i.e. prior to the implantation of the embryo. Furthermore, juvenile diabetes can, with the method of the present invention, be diagnosed via amniocentesis. The early diagnosis of juvenile diabetes in accordance with all applications of the method of the invention allows for treatment directly after birth before the onset of clinical symptoms.

In a particularly preferred embodiment of the method of the invention, said testing for differentiation status in said β-cells is carried out in an embryonic or newborn mammal.

As has been indicated hereinabove, it is particularly preferred to include at least one further step in the method of the invention, which is specific for different pharmaceutical and genetic therapeutic approaches. As mentioned above, different small pharmaceutically active molecules could be used to activate Pax4 and optionally Pax6 expression and therefore induce differentiation and production of insulin producing β-cells. Likewise, intracellular targeting of active Pax4 and/or optionally Pax6 would advance similar consequences. In accordance with this statement, pancreatic ductal epithelial cells have been proposed to contain potential stem cells for endocrine cell types. Induction of Pax4 activity in said cells but not exclusively in said cells can promote differentiation into insulin producing cells (Parsa et al, 1985, Cancer Res. 45:1285–1290).

In a further preferred embodiment of the method of the invention, said differentiation status of pancreatic cells is the result of the activity of a medicament or of a gene therapy approach. For example, said differentiation status may be influenced by gene therapy approaches where a functional Pax4 and optionally Pax6 gene is introduced in vivo into cells using a retroviral vector (Naldini et al., Science 272 (1996), 263–267; Mulligan, Science 260 (1993), 926–932) or another appropriate vector. Likewise, in accordance with the present invention cells from a patient can be isolated, modified in vitro to differentiate into β-cells using standard tissue culture techniques and reintroduced into the patient.

In a particularly preferred embodiment, said medicament or gene therapy approach affects the expression level of the Pax4 gene and, optionally, of the Pax6 gene at the mRNA or protein level.

The above embodiments of the present invention allow, inter alia, testing of a medicament for its influence on expression of the aforementioned Pax genes. As has been stated further hereinabove, abnormal expression levels of Pax4 and optionally of Pax6 are expected to be a causative agent in the generation of, for example, solid tumors of the pancreas. The method of the invention thus allows the testing of medicaments, the application of which would allow the cell to return to a normal expression level. Said normal expression level would be expected to have a direct influence on, e.g., the malignancy of a cell. For example, if a disease or tumor is a direct or indirect result of an under-expression of Pax4, the physician treating the respective patient would administer a medicament that stimulates expression of Pax4.

In a further preferred embodiment of the method the invention, the testing for differentiation status in pancreatic cells is a testing for the developmental status in Pax4 knockout mice that are optionally at the same time Pax6 knockout mice.

In an additional preferred embodiment of the method of the present invention, said method further comprises introducing a functional and expressible Pax4 gene and optionally further comprising introducing a functional and expressible Pax6 gene into pancreatic α-cells or ductal epithelial cells which possess a similar yet different differentiation pathway as compared to β-cells. With this embodiment of the invention, the person skilled in the art is in the position to redirect the fate of α-cells or ductal epithelial cells into β-cells. Thus, α-cells are expected to differentiate after transfection with the Pax4 gene and optionally the Pax6 gene into β-cells. A corresponding pharmaceutical application is envisaged, if a patient suffers from a β-cell- and thus insulin deficiency. It is envisaged that this method is carried out in vitro or in vivo.

The present invention further relates to a transgenic mammal comprising at least one inactivated Pax4 allele. As to research uses of the transgenic mammal especially, it is preferred that the mammal be non-human.

The transgenic animal of the present invention can advantageously be used for monitoring the development of different cells, for example, in the pancreas. However, the use of the transgenic mammal is not confined to the study of pancreatic development. Since Pax4 is, in accordance with the present invention, now believed to be a master regulator for β-cells, its influence can also be studied in other cell types of the body.

Since the transgenic animal of the invention which is preferably a transgenic mouse in the homozygous state has severe pancreatic disorders that, in the case of transgenic mice, lead to death within three days after birth, said transgenic animal can further be used for the investigation of diseases associated with developmental disorders, in particular in the pancreas. Since the transgenic mice are deficient in insulin producing cells and present clinical symptoms similar to human patients suffering from juvenile diabetes, said mice can serve has an animal model for therapeutic and pharmaceutical research against juvenile diabetes.

Preferably, the transgenic mammal of the invention further comprises at least one inactivated Pax6 allele.

This embodiment allows the study of the interaction of Pax4 and Pax6 on the development of the mammal or certain tissues thereof, in particular, of the pancreas. All the applications that have been herein before discussed with regard to the Pax4 transgenic mammal also apply to the mammal that carries two transgenes. It might be also desirable to inactivate Pax4 gene expression and optionally Pax6 gene expresssion at a certain stage of development and/or life of the transgenic animal. This can be achieved by using, e.g., tissue specific developmental and/or cell regulated and/or inducible promoters which drive the expression of, e.g., an antisense or ribozyme directed against the RNA transcript encoding the Pax4 protein and optionally to the Pax6 encoding RNA. A suitable inducible system is for example the tetracycline-regulated gene expression as described, e.g., by Gossen and Bujard (Proc. Natl. Acad. Sci. 89 USA (1992), 5547–5551) and Gossen et al. (Trends Biotech. 12 (1994), 58–62).

In another preferred embodiment of the invention said transgenic mammal is human, a mouse or a rat. Since at least one inactivated Pax4 allele can be introduced into a mammal for therapeutic applications, as discussed above, the transgenic mammal can be human.

In accordance with the present invention, the transgenic animal may be homozygous or heterozygous for either inactivated Pax4 or inactivated Pax6 or for both inactivated genes.

Moreover, the present invention relates to the use of at least one first nucleic acid sequence encoding a functional and expressible Pax4 protein and optionally a second nucleic acid sequence encoding a functional and expressible Pax6 protein for the preparation of a pharmaceutical composition for treating, preventing and/or delaying diabetes in a mammal. According to the invention, vectors containing said nucleic acid sequences may be operatively linked to regulatory elements allowing for expression of said nucleic acid sequences and/or for targeting of said nucleic acid sequences to pancreatic cells.

Further, the invention relates to the use of a functional Pax4 protein and optionally a functional Pax6 protein for the preparation of a pharmaceutical composition for the treatment, prevention and/or delay of diabetes and/or a neuronal disorder in a mammal. The term "functional" bears the same meaning as outlined hereinabove.

Preferably, the mammal referred to in the above embodiments is a human, a rat or a mouse. And thus, the invention further comprehends a transgenic mammal modified so as to comprise at least one first nucleic acid molecule comprising a sequence encoding a functional and expressible Pax4 protein and optionally a second nucleic acid molecule comprising a sequence encoding a functional and expressible Pax6 protein (wherein the mammal has expression of the nucleic acid molecule(s)). The mammal can be modified pre-natally or post-natally, e.g., after a method of the present invention shows low, impaired or no Pax4 protein or mRNA, for treatment, prevention or delaying diabetes; and, the modification can be by techniques discussed herein or by techniques within the ambit of the skilled artisan, without undue experimentation from this disclosure.

It is envisaged by the present invention that the nucleic acids and proteins are administered either alone or in any combination, and optionally together with a pharmaceutically acceptable carrier or excipient. Said nucleic acid sequences may be stably integrated into the genome of the mammal. On the other hand, viral vectors may be used which are specific for certain cells or tissues, preferably pancreas and/or brain, and which persist in said cells thereby conferring expression of the Pax genes in said cells. Suitable pharmaceutical carriers and excipients are well known in the art. Elements capable of targeting a nucleic acid molecule and/or protein to specific cells are described in the prior art, for example in, Somia et al., Proc. Natl. Acad. Sci. USA 92 (1995), 7570–7574. The pharmaceutical compositions can be administered to the mammal at a suitable dose, which can be determined from this disclosure and knowledge in the art, without undue experimentation by the skilled artisan taking into consideration typical factors such as the species, age, sex, weight, condition of the mammal, the route of administration, whether a Pax4 protein or Pax4 and Pax6 proteins are being administered, whether an agent for inhibiting or stimulating Pax4 or Pax4 and Pax6 is being administered, whether a nucleic acid or acids are being administered, and whether the nucleic acid or acids are for expression of Pax4 or Pax4 and Pax6 or are for inhibiting expression of Pax4 or Pax4 and Pax6, inter alia. A typical dose can be, for example, in the range of 0.001 to 1000 µg (or of nucleic acid for expression or for inhibition of expression in this range); however, doses below or above this exemplary range are envisioned, especially considering the aforementioned factors.

Administration of the suitable compositions may be effected in different ways, e.g., by intravenous, intraperitoneal, subcutaneous, intramuscular, topical or intradermal administration. The pharmaceutical compositions prepared according to the invention can be used for the prevention or treatment or delaying of different kinds of diseases, for example, pancreas related diseases, namely diabetes or different kinds of acquired or in-born neural disorders, neural degenerations and related disorders. Said diseases and disorders are preferably derived from endocrine or neural tissues, e.g. pancreas and brain.

Furthermore, it is possible to use a pharmaceutical composition which comprises a nucleic acid sequence which encodes a Pax4 protein and optionally a nucleic acid sequence encoding a Pax6 protein for gene therapy. Naturally, both sequences may also be comprised in the same vector. As described above, the diseases often evolve when cells lose both functional copies of the Pax genes. In such a case, introduction of functional copies of the corresponding gene may help to ameliorate the situation. For example, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. In genetic diseases the introduction of a normal or a functionally adequate allele of a mutated nuclear gene represents gene replacement therapy, which is applicable mainly to monogenetic recessive disorders such as, for example, diabetes and hypoglycemia.

Thus, in a further embodiment, the invention relates to a method for treating diabetes comprising:
  (a) removal of a cell from a mammal;
  (b) introduction of a functional and expressible Pax4 gene and optionally a functional and expressible Pax6 gene into said cell; and
  (c) reintroducing the cell obtained as a product of step (b) into said mammal or into a mammal of the same species.

Yet, in a further embodiment, the invention relates to a method for treating a neuronal disorder comprising:
  (a) removal of a cell from a mammal;
  (b) introduction of a functional and expressible Pax4 gene and optionally a functional and expressible Pax6 gene into said cell; and (c) reintroducing the cell obtained as a product of step (b) into said mammal or into a mammal of the same species.

It is to be understood that the introduced genes are functional and expressible after introduction into said cell and preferably remain in this status during the lifetime of said cell.

Preferably, said mammal is a human, a rat or a mouse.

In a preferred embodiment of the method of the invention, said cell is a germ line cell or embryonic cell or derived therefrom. In a further preferred embodiment, said cell is an egg cell or derived therefrom.

Suitable vectors and methods for in-vitro or in-vivo gene therapy are described in the literature and are known to the person skilled in the art. The pharmaceutical compositions according to the invention can be used for the treatment of kinds of diseases hitherto unknown as being related to the expression and/or non-expression of the Pax4 gene and/or the Pax6 gene.

BRIEF DESCRIPTION OF THE DRAWINGS

This disclosure may best be understood in conjunction with the accompanying drawings, incorporated herein by reference, which show.

b, DNA isolated from ES cell clones was digested with SpeI and analyzed by Southern blot hybridization with both, a 0.7 kb external genomic fragment (probe 1, left), and a 0.5 kb cDNA fragment (probe 2, right). Sizes are in kilobases. In both, the 26 kb fragment is indicative of the wild-type allele, while the 20 kb and the 7.8 kb fragments, respectively, originate from the targeted allele. Asterisks indicate two clones positive for homologous recombination.

c, A pair of 2 days-old littermates, wild-type (upper) and Pax4-deficient (lower), showing the reduced size of the null-mutant mouse.

d, Embryos were genotyped by PCR analysis using genomic DNA from yolk sacs or tails, and two sets of primers (located as shown by arrows in a), in order to amplify wildtype-paired domain and/or, the neo gene.

Figure 1A:
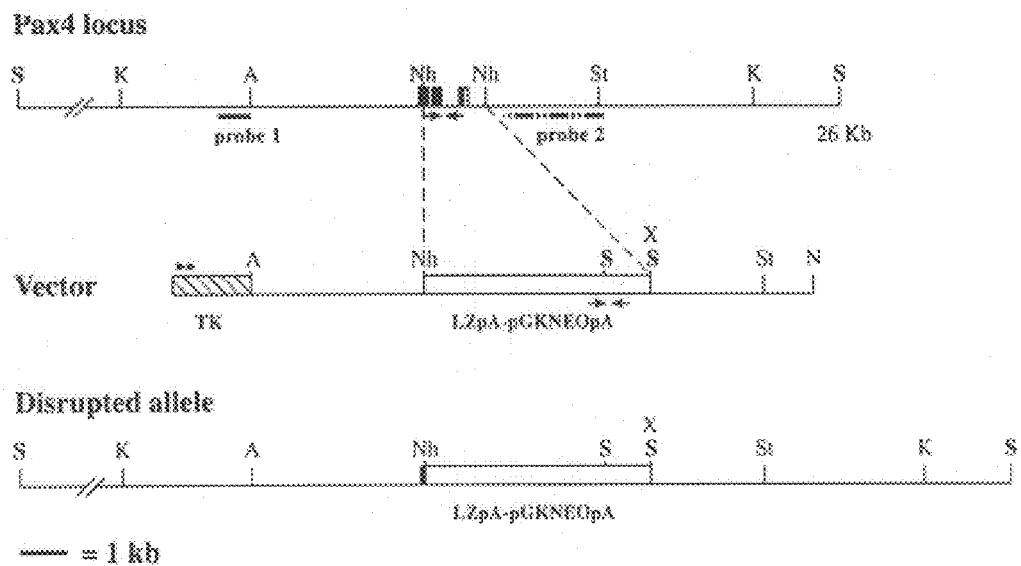
FIG. 1 (FIGS. 1a, 1b, 1c, 1d). Targeted disruption of Pax4 and generation of Pax4 (−/−) mice a, structure of the wild-type and targeted Pax4 loci. A targeted deletion of almost all the entire paired box domain (dark boxes; exons 2, 3 and 4) of Pax4 was produced, by fusing in frame a β-galactosidase-neomycin resistance cassette (transcription direction is indicated by double arrowheads). Restriction enzymes: A, ApaI; K, KpnI; Nh, NheI; N, NotI; S, SpeI; St, StuI; X, XhoI.
Figures 1, 1B, 2:
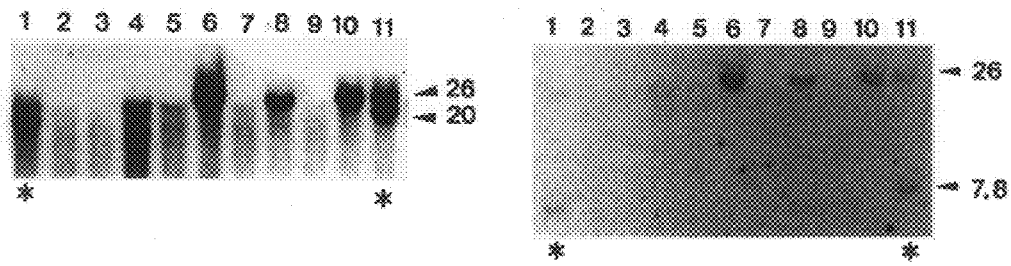

FIG. 2 (FIGS. 2a, 2b, 2c, 2d, 2e, 2f, 2g, 2h). Analysis of LacZ activity, insulin and glucagon expression, in the pancreas of Pax4 (+/−) and Pax4 (−/−) E16.5 embryos and newborn mice In E16.5 (+/−) pancreas, insulin (arrow in a) and glucagon (arrow in b) cells are associated with regions where LacZ activity (arrowheads in a and b) is detected. In contrast, in the pancreas of E16.5 (−/−) embryos, expression of LacZ (arrowheads in e) is diminished, whereas insulin is absent (compare a and e). In E16.5 (−/−) pancreas a larger number of glucagon-cells is found (arrow in f), associated with regions of LacZ activity (arrowhead in f). In (+/−) newborn pancreas, LacZ expression is restricted to insulin cells (arrow in c), and appears surrounded by the glucagon-cells (arrow in d). In (−/−) newborn pancreas, no expression of LacZ activity or insulin is detected (compare c, d and g). Meanwhile, in (−/−) newborn pancreas, numerous glucagon-cells are present (arrow in h), also abnormally distributed in clusters (compare d and h). Magnification is 400×.

Figure 3E:
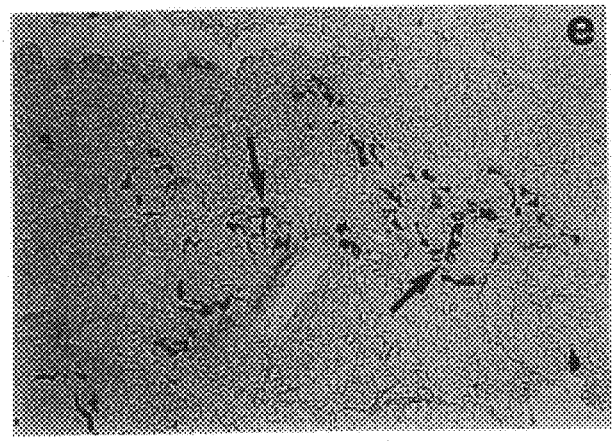
Figure 3F:
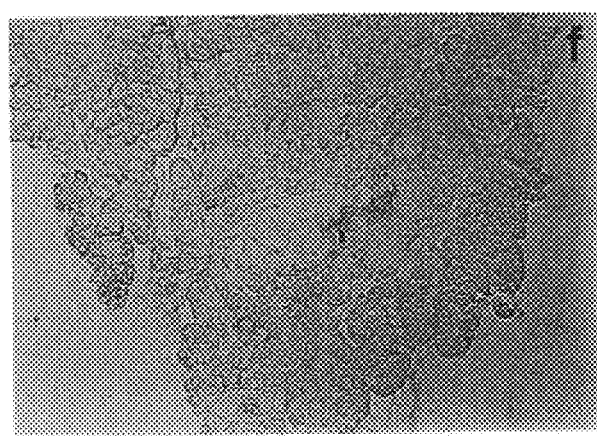

FIG. 3 (FIGS. 3a, 3b, 3c, 3d, 3e, 3f). Expression of Pdx1 and somatostatin in Pax4 (+/+) and (−/−) newborn pancreas.

In the dorsal pancreas of both, (+/+) and (−/−) E10.5 embryos, the early expression of Pdx1 looks similar (compare a and b).

In newborn (+/+) pancreas, Pdx1 is restricted to mature insulin-producing β-cells (arrows in c). In the pancreas of Pax4 (−/−) newborn mice, no expression of Pdx1 is detected (compare c and d). In (+/+) newborn pancreas, somatostatin producing δ-cells are mainly distributed within the cells that surround the Islets of Langerhans (arrows in e). In (−/−) newborn pancreas, however, somatostatin is not detected (compare e and f). a and b are vibratome sections. c and d are cryostat sections. e and f are paraffin sections. Magnification in (c–f) is (200×), and in a and b is (400×).

FIG. 4 (FIGS. 4a, 4b, 4c, 4d). Histological analysis of Pax4 (+/+) and (−/−) pancreas from newborn mice, and expression of α-amylase Exocrine acini are shown in (a), containing groups of pyramidally-shaped cells (arrowheads), with their nuclei at the base. Exocrine cells are also present in newborn (−/−) pancreas (arrowheads). However, extensive areas of cytoplasm are observed, as well as a disorganized distribution of their nuclei (compare a and b). In the (+/+) newborn pancreas, exocrine cells contain different amounts of α-amylase (arrows and arrowhead in ac), reflecting the depletion of digestive enzymes that normally follows suckling. In almost all the exocrine tissue of newborn (−/−) pancreas, however, a large amount of α-amylase is present (arrows in e), indicating that its secretion might be affected. Magnification in a and b is (400×), and in c and d is (200×).

Figure 5:
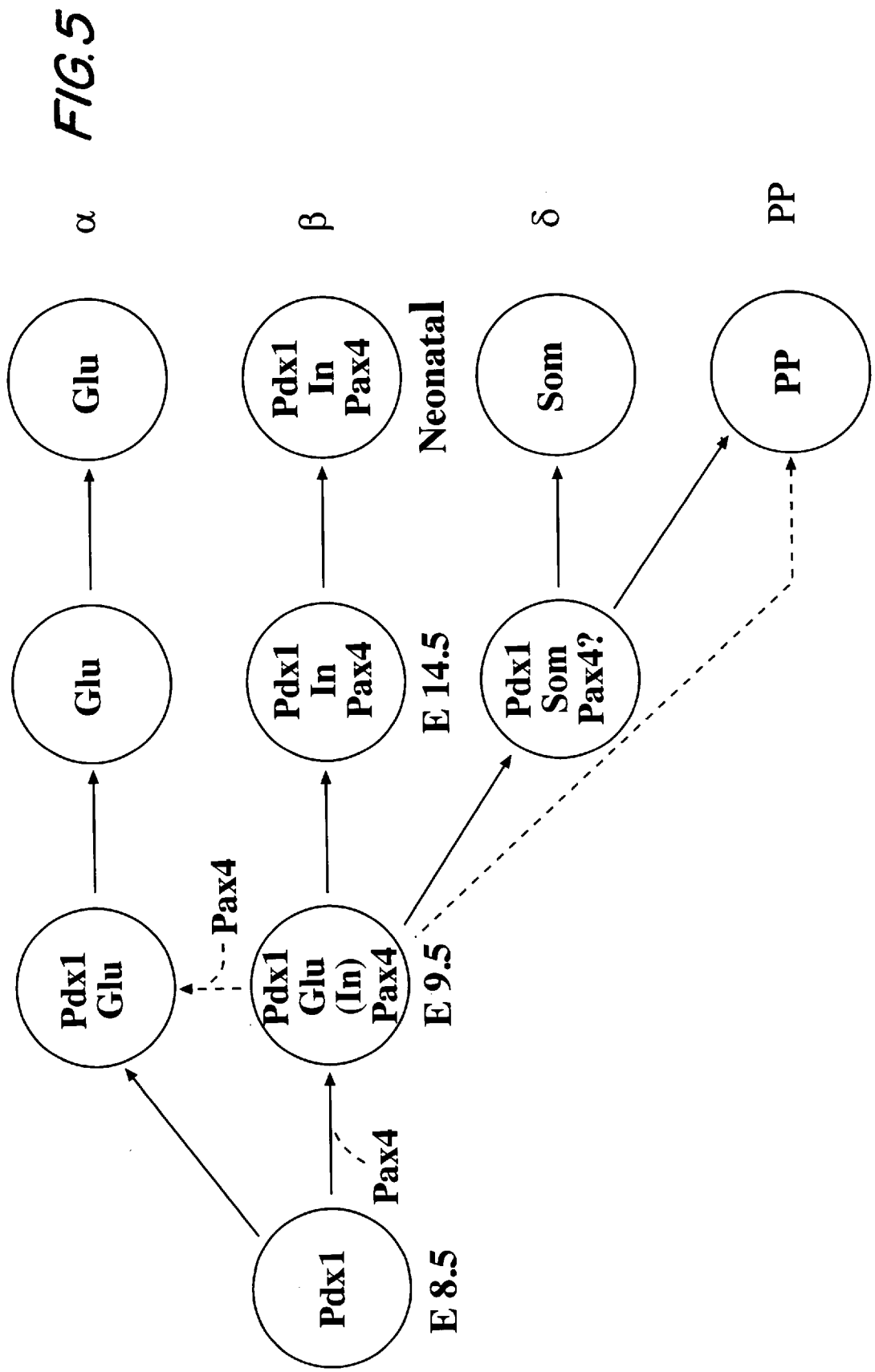

FIG. 5. Model for the role of Pax4 in endocrine differentiation, in the mouse pancreas.

Earliest endocrine progenitor cells are characterized by their expression of Pdx1, at around E8.5 of mouse development (Guz et al., Development 121 (1995), 11–18). Differentiation of α-cells occurs very early in development, in precursors in which presumably Pdx1 is no longer present. In the earliest β-cell progenitors, genes like Pdx1 and insulin are selectively expressed, and maintenance of their expression seems important for their progression into differentiation. In mature endocrine cells: Pdx1, insulin and Pax4 have their expression restricted to the β-lineage. Pax4 may promote and/or maintain the expression of genes specific for the insulin-producing β-cells.

FIGS. 6 to 21. Sequences 1 to 15 (identified below by SEQ ID No.).

A better understanding of the present invention and of its many advantages will be had from the following examples, given by way of illustration.

EXAMPLES

Antibodies used against insulin, glucagon and amylase are commercially available from several companies. The antibodies used in Applicants' experiments were purchased from Boeringer Mannheim. The Pdx1 antibody was a generous gift from Prof. Thomas Edlund (Department of Microbiology, University of Umea, S-901 87 Umea, Sweden). Antibodies with the same specificity i.e. which specifically recognize the Pdx1 protein can be prepared using the Pdx1 protein as an antigen according to conventional procedures.

EXAMPLE 1

Preparation of Construct for Homologous Recombination and Generation of Pax4-Deficient Mice Targeted deletion of almost all the entire paired box domain (dark boxes; exons 2, 3 and 4) of Pax4 was produced, by fusing in frame a β-galactosidase-neomycin resistance cassette. A 5.1 kb Xba-Xhol fragment containing LacZpA-pGKNeopA sequences was blunt ended and ligated into the NheI-digested and blunt ended Pax4 construct. The LacZpA-pGKNeopA construct was made by combining the pGKneo plasmid (Soriano et al., 1991, Cell 64:693–702) and the β-galactosidase gene which is available from several commercial sources (e.g. pCH110 vector from Pharmacia). The 5' NheI site was retained and a new SpeI site was generated at the 3' end. A F9 polyoma early promoter derived HSV TK gene was added upstream to the 5' homology, for negative selection. R1 ES-cells were electroporated and selected following standard procedures. Positive clones were used to generate chimeras by morula aggregation. Tail and yolk sac DNA-isolation and PCR amplification of genomic DNA were performed using standard procedures. Analysis of the phenotype was done in NMR1 and C57BL/6 mice. No differences were observed between both genetic backgrounds.

EXAMPLE 2

Studies on the Expression of Pax4 During Development

A genomic screen has previously identified Pax4 as a member of the murine family of Pax genes (Walther et al., Genomics 11 (1991), 424–434). By RT-PCR Applicants isolated the corresponding cDNA sequence.

PCR amplification of a fragment (615 nt) encoding the paired and homeobox domains of Pax4 cDNA was done with 1 mg of total RNA isolated from E13.5 mouse embryos. Reverse transcription was performed with a kit from Pharmacia, and random primers. Primers used were obtained after sequencing the corresponding genomic regions encoding the paired (5', sense primer: 5' AGC AAT AAG AGG GAT GCG ACC 3' (SEQ ID No. 5)) and homeobox (3', antisense: 5' AGC TGT GCT TCC CAT TTC AGC 3' (SEQ ID No. 6)) domains, respectively. In all the PCR reactions that were performed (including 5' and 3' RACE), Taq polymerase was added after the first denaturation step (95° C., 3 min), before cycling proceeded. 2 units of Taq polymerase together with 1 unit of "Perfect Match" (from Stratagene) were added. 35 cycles were performed: 95° C., 1½ min; 60° C. 1½ min; 72° C. 2½ min. A final step with: 60° C., 1½ min and 72° C. for 10 min was performed. A faint band with the expected size was seen after gel electrophoresis in 2% low-melting agarose. This was excised and reamplified (5 ml of molten agarose) with the same program. DNA was electroeluted from a 2% preparative gel, filled-in and blunt-end cloned into Bluescript digested with SmaI, following standard procedures. Sequencing of the isolated clones was done with a sequencing kit from Pharmacia. 5'-RACE amplification was performed using a kit from GIBCO-BRL, following manufacturer's instructions. Briefly, 5 mg of total RNA isolated from the posterior region of E10.5 mouse embryos (posterior to the hindlimb bud: "tail-RNA") was used as template for first-strand cDNA synthesis. Two sets of nested primers were used in combination with the AP (primer BS41: 5' GCG AAT TCC CTG AAG TGC CCG AAG TAC TCG ATT 3' (SEQ ID No. 7)) and UAP (primer BS57: 5' GGC TCC GTG AAA TGT CAC AG 3' (SEQ ID No. 8)) primers, respectively. In the first PCR reaction, one primer specific for Pax4 located close to the 5' region of its known sequence was used in conjunction with the "AP" primer 5° CGT AGT ACT GTC GAC TAG CAG GGI IGG GII GGG IIG 3' (SEQ ID No. 9) from the commercially available kit (5' Race system from GIBCO-BRL). The "AP" primer contains an adaptor linked to a dG-tail which anneals to the dC-tailed cDNA. For the second reaction, a "nested" Pax4 primer ("nested meaning located more 5' or 'upstream' to the Pax4 primer used in the first reaction) was used together with the commercial "UAP" primer (primer that contains only the adaptor sequence of the AP primer 5° CGT AGT ACT GTC GAC TAG CA 3' (SEQ ID No. 10). First PCR (AP/BS41 primers) was performed with 5 ml of dC-tailed cDNA (35 cycles of: 94° C., 1½ min; 55° C., 1½ min; 72° C., 3 min). 2 ml of this resulting PCR reaction (diluted 20 times) were reamplified with primers UAP/BS57, and 40 cycles of: 94° C., 1 min; 60° C., 1 min; 72° C., 2½ min. A single band of approximately 500 nt was seen after gel electrophoresis. This was electroeluted and cloned into the TA-pGEM vector (PROMEGA). 180 nt of 5' new sequence information was obtained with this approach. 3' RACE amplification was done using 2.5 mg of "tail" E10.5 RNA as template. First-strand cDNA synthesis was performed with the NotI-oligo dT primer provided by the First-strand cDNA synthesis kit (Pharmacia). First PCR was performed with the NotI primer (5' AAC TGG AAG AAT TCG CGG CCG CAG GAA 3' (SEQ ID No. 11)) and BS36 (5° CAG GAA GAC CAG AGC TTG CAC TGG 3' (SEQ ID No. 12)) primers. 35 cycles (94° C., 1½ min; 55° C., 1½ min; 72° C., 3 min) were performed. 2 ml of this PCR reaction (diluted 20 times) were reamplified with a nested primer (BS42: 5' GCG GAT CCC ACA GGA ATC GGG CTA TCT TC 3' (SEQ ID No. 13)) and NotI primer. After gel electrophoresis, a prominent band of approximately 550 nt was excised from a 2% low-melting agarose gel. 2 ml of molten agarose were reamplified with another nested primer (BS59: 5' GCG CAG GCA AGA GAA GCT GA 3' (SEQ ID No. 14)) and NotI primer. The last two PCRs were: 40 cycles of: 60° C., 1½ min; 72° C., 3 min; 94° C., 1½ min. A 420 nt prominent band was electroeluted and subcloned into TA-pGEM vector. The fidelity of the amplified 5' and 3'-PCR fragments was assessed by two procedures: first, a 1.1 kb fragment was amplified from "tail" E10.5 RNA, using primers (sense primer: 5' CTT CCA GAA GGA GCT CTC 3' (SEQ ID No. 15) and its antisense primer: 5' TGG GAT GAT GGC ACT TGT C 3' (SEQ ID No. 16)) designed from the most 5' and 3' newly sequences. Its size and sequence were as expected. Also, the sequence of the three PCR-isolated fragments (5'-, 615 nt and 3'-) was compared with the equivalent coding regions in a genomic clone.

Analysis of Pax4 expression revealed that its transcripts are restricted to a few cells in the ventral spinal cord and the early developing pancreas. In order to investigate the function of this gene during development, Applicants generated Pax4-deficient mice; see Example 1. Inactivation of Pax4 after homologous recombination in ES-cells was achieved, after deleting almost the entire paired box domain, and fusing the β-galactosidase gene in frame with the amino-terminus of Pax4 (FIG. 1a). This approach also allowed Applicants to analyze in more detail the expression of Pax4 throughout development, by detection of LacZ activity.

Figure 1C:
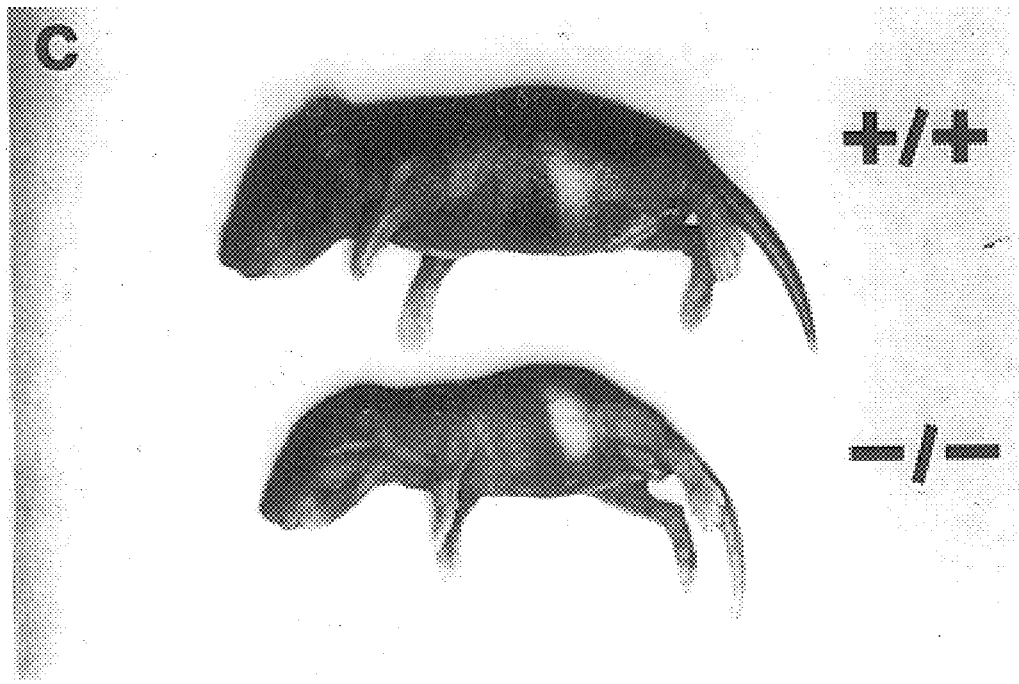
Figure 1D:
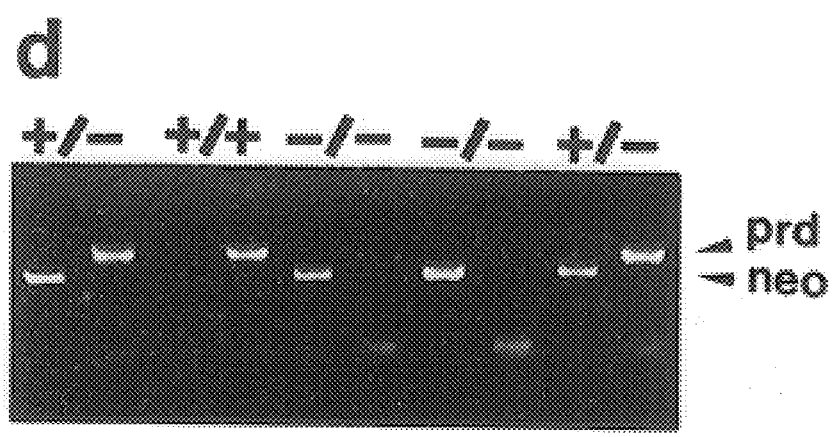

Heterozygous mice do not exhibit any obvious abnormalities and they are viable and fertile. Staining of (+/−) embryos at day 10.5 of development (E10.5), revealed LacZ activity in cells within the dorsal pancreas. For detection of LacZ activity, X-gal staining of mouse embryos and isolated newborn pancreas was performed, following standard procedures. A post-fixation was performed in 4% paraformaldehyde, at 4° C., overnight. For immunohistochemistry, X-gal stained embryos and tissues were embedded in paraffin, and sectioned (10 $\mu$M) with a microtome. Expression of LacZ in the pancreas of Pax4 (+/−) embryos proceeded until birth. In heterozygous newborn pancreas, LacZ activity was found restricted to discrete areas corresponding to the β-cells in the Islets of Langerhans, as judged by co-expression of LacZ and insulin (FIGS. 1c and d).

Pax4-deficient offspring were born with the expected Mendelian distribution, indicating that the absence of Pax4 is not lethal in utero. At birth, Pax4 (−/−) mice appear normal and were indistinguishable from their littermates. However, 48 hours later they exhibited growth retardation and dehydration (FIG. 1c). All Pax4-deficient mice died within the first three days after birth, demonstrating the complete penetrance of the mutant phenotype. Pancreas of newborn Pax4 (−/−) mice showed a normal macroscopical appearance. The expression of LacZ in the pancreas of Pax4 (−/−) mutant mice was also investigated. In E10.5 (−/−) embryos LacZ activity was detected in cells of the dorsal pancreas, in a similar manner to heterozygous embryos. No differences in the expression of LacZ activity were observed in the developing pancreas of Pax4 (+/−) and (−/−) embryos, until approximately E16.5. After this, however, in the pancreas of Pax4-deficient mice LacZ expression began to diminish (compare FIGS. 2a, b and 2e, f), and it became undetectable after birth (compare FIGS. 2d and 2g).

EXAMPLE 3

Expression of Insulin and Glucagon in Pax4 Targeted Mice

In the pancreas, all endocrine cells arise from common multipotent precursors (Alpert, Cell 53 (1988), 295–308). The first precursor cells containing insulin and glucagon, appear around E9.5 (Gittes et al., Proc. Natl. Acad. Sci. USA 89 (1992), 1128–1132; Teitelman et al., Development 118 (1993), 1031–1039). In the mouse pancreas, differentiation of exocrine and most endocrine cells starts around E16.5 of development (Githens, The Pancreas: biology, pathobiology, and disease. Second Edition (ed. Vay Liang W. Go, et al.) Raven, N.Y., (1993), 21–73). At birth, insulin production is mostly restricted to fully differentiated β-cells, located in the center of the islets of Langerhans. These are surrounded by the glucagon-producing α-cells. β-cells comprise the majority of the endocrine population, whereas the α-cells represent only a small fraction (Slack, Development 121 (1995), 1569–1580). Applicants have tested for the expression of insulin and glucagon in the pancreas of Pax4 heterozygous and Pax4 null-mutant mice, by immunochemistry on paraffin sections performed as previously described (Oliver et al., EMBO J. 7 (1988), 3199–3209).

At E10.5, insulin-producing cells were detected in the pancreas of Pax4 (+/−) and (−/−) embryos. In E16.5 heterozygous embryos, all insulin cells were found included within the area of LacZ activity (FIG. 2a). As previously mentioned, in heterozygous newborn mice LacZ and insulin were detected in the same cells (FIG. 2c), indicating that later in development Pax4 expression is restricted to the insulin-producing β-cells. In contrast, in the pancreas of Pax4 (−/−) E16.5 embryos and newborn mice, few if any insulin-producing cells were detected (FIG. 2e, g). This indicates that in the absence of Pax4, the maturation of the pancreatic β-cells was affected. In the pancreas of E10.5 (+/−) and (−/−) embryos, cells containing glucagon are present. In heterozygous E16.5 embryos, glucagon was detected in cells, most of which were contained within the area of LacZ activity (FIG. 2b). In newborn heterozygous pancreas, glucagon was present in cells surrounding the area where the LacZ was expressed, but were not included within it (FIG. 2d). In the pancreas of Pax4 (−/−) E16.5 embryos and newborn mice, a considerably larger number of glucagon-producing cells was found. These cells also showed an aberrantly clustered distribution (FIGS. 2f and h).

EXAMPLE 4

Expression of Pdx1 in Pax4 Targeted Mice

In order to further confirm that in the pancreas of Pax4-deficient newborn mice β-cells are missing, the expression of a specific β-cell marker, Pdx1, was tested. This gene appears very early in pancreas development (most likely in the earliest pancreatic progenitors), but later becomes restricted to the fully differentiated β-cells (Guz et al., Development 121, 11–18 (1995); Miller et al., EMBO J. 13 (1994), 1145–1156) (FIG. 3c). Its early expression was assayed by whole-mount immunostaining of E10.5 mouse embryos, using an established protocol (Ohlsson et al., EMBO J. 13 (1994), 1145–1158), except that bleaching was for 24 hours. After staining, E10.5 embryos were postfixed, embedded in a gelatin-BSA matrix and sectioned with a vibratome. Expression of Pdx1 in newborn pancreas by immunostaining on cryostat sections was performed as previously described, with the following modifications: newborn pancreas was fixed 3 hours with 4% paraformaldehyde, and then cryoprotected with 30% sucrose in PBS, overnight. After washing-off the secondary antibody, secretions were incubated with 0.6% $H_2O_2$, 20 min. At E10.5, Pdx1 was similarly expressed in the pancreas of both, Pax4 (+/+) and (−/−) embryos (FIGS. 3a,b). However, in the pancreas of Pax4-deficient newborn mice, Pdx1 expression was not detected. This confirms the initial conclusion that, in the pancreas of Pax4 null-mutant mice, the mature β-cells are absent. It also suggests that, although Pax4 may not be required for generation of the earliest endocrine precursors, it is crucial for β-cell differentiation.

EXAMPLE 5

Expression of Somatostatin in Pax4 Targeted Mice

During mouse embryogenesis, somatostatin-producing cells start to differentiate later than α- and β-cells (Teitelman et al., Development 118 (1993), 1031–1039). In the pancreas of Pax4 (+/+) newborn nice, somatostatin-producing δ-cells were mainly distributed in the periphery of islets, intermingled with the α-cells (FIG. 3e), suggesting that inactivation of Pax4 also affected the maturation of the δ-lineage. Expression of somatostatin in the gut, however, appeared unaffected.

EXAMPLE 6

Histological Analysis of Newborn Pancreas From Pax4 Targeted Mice

Figure 4A:
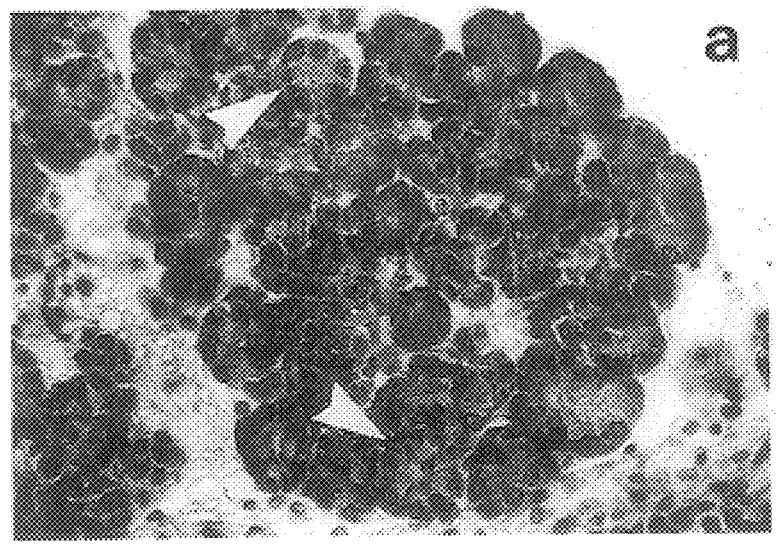
Figure 4C:
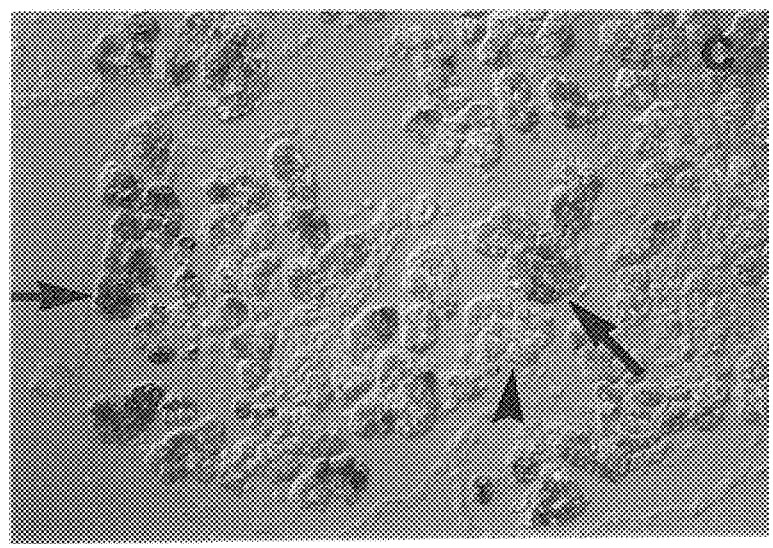
Figure 4B:
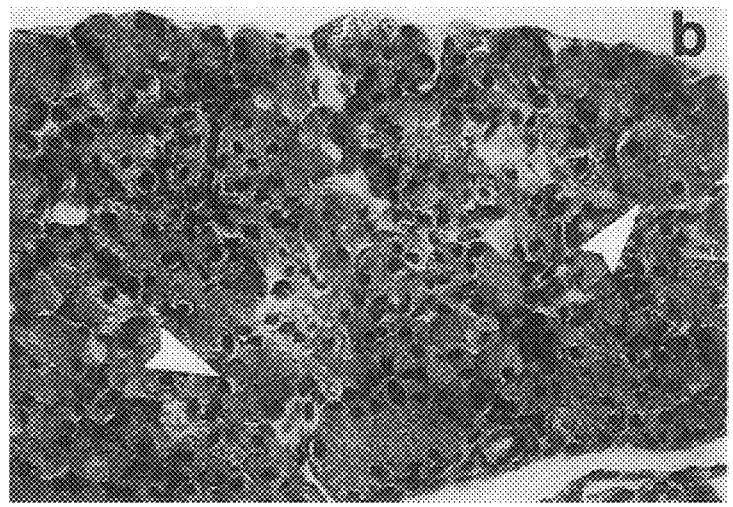
Figure 4D:
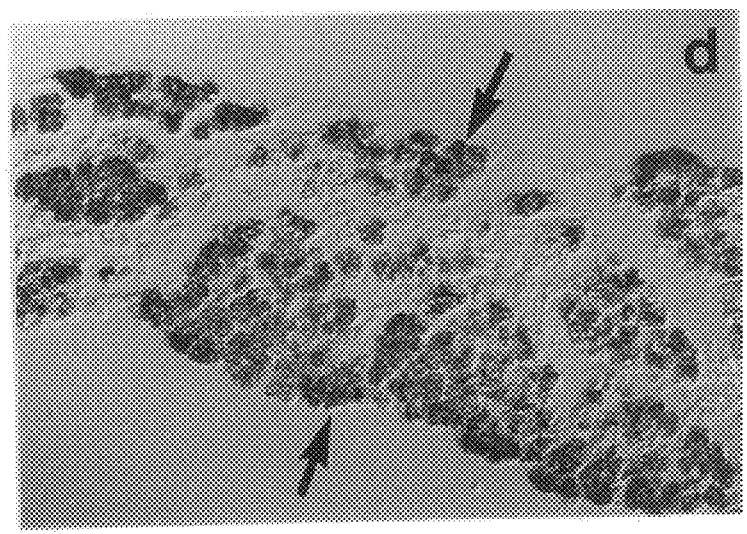

Exocrine pancreas is a lobulated, branched, acinar gland, with pyramidal-shaped secretory cells and basal nuclei (Pictet, Devl. Biol. 29 (1972), 436–436) (FIG. 4a). Histological analysis of newborn Pax4 (−/−) pancreas showed that in this gland, exocrine tissue was present. However, the cytoplasm of exocrine cells seemed expanded, and their nuclei did not show a homogenously basal distribution (FIG. 4b). When pancreas of 3-days old wildtype mice was analyzed for the presence of a specific exocrine enzyme (α-amylase), large portions of exocrine tissue showed little or no expression of such marker (FIG. 4c). This most likely reflects the depletion of exocrine digestive enzymes that normally occurs after suckling (Githens, The Pancreas: biology, pathobiology, and disease. Second Edition (ed. Vay Liang W. Go, et al.) Raven, N.Y., (1993), 21–73). At birth, Pax4-deficient mice are able to suckle, since their stomachs are full with milk (FIG. 1c). However, 3-days old Pax4 (−/−)

pancreas showed a strong expression of α-amylase in all exocrine cells, indicating that they might not be able to secrete their enzymes into the digestive tract (FIG. 4d).

The conclusions to be drawn from the results of the above examples with respect to the influence of the Pax4 and Pdx1 genes on the development of pancreatic cells is shown in FIG. 5.

Having thus described in detail preferred embodiments of the present invention, it is to be understood that the invention defined by the appended claims is not to be limited by particular details set forth in the above description as many apparent variations thereof are possible without departing from the spirit or scope thereof.

```
                           SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "oligonucleotide"

(ix) FEATURE:
        (A) NAME/KEY: CDS
        (B) LOCATION:166..1161

(xi) SEQUENCE DESCRIPTION: SEQ ID NO: 1:

ACCAGCAACC CTGGAGCCTG CACAGACCCT GAGACCTCTT CCTGAATTCC CACCTTTTTT         60

CCTCCATCCA GTACCAGTCC CAAAGAGAAA CTTCCAGAAG GAGCTCTCCG TTTTCAGTTT        120

GCCAGTTGGC TTCCTGTCCT TCTGCGAGGA GTACCAGTGT GAAGC ATG CAG CAG           174
                                                 Met Gln Gln
                                                   1

GAC GGA CTC AGC AGT GTG AAT CAG CTA GGG GGA CTC TTT GTG AAT GGC        222
Asp Gly Leu Ser Ser Val Asn Gln Leu Gly Gly Leu Phe Val Asn Gly
  5                  10                  15

CGG CCC CTT CCT CTG GAC ACC AGG CAG CAG ATT GTG CAG CTA GCA ATA        270
Arg Pro Leu Pro Leu Asp Thr Arg Gln Gln Ile Val Gln Leu Ala Ile
 20                  25                  30                  35

AGA GGG ATG CGA CCC TGT GAC ATT TCA CGG AGC CTT AAG GTA TCT AAT        318
Arg Gly Met Arg Pro Cys Asp Ile Ser Arg Ser Leu Lys Val Ser Asn
                 40                  45                  50

GGC TGT GTG AGC AAG ATC CTA GGA CGC TAC TAC CGC ACA GGT GTC TTG        366
Gly Cys Val Ser Lys Ile Leu Gly Arg Tyr Tyr Arg Thr Gly Val Leu
             55                  60                  65

GAA CCC AAG TGT ATT GGG GGA AGC AAA CCA CGT CTG GCC ACA CCT GCT        414
Glu Pro Lys Cys Ile Gly Gly Ser Lys Pro Arg Leu Ala Thr Pro Ala
         70                  75                  80

GTG GTG GCT CGA ATT GCC CAG CTA AAG GAT GAG TAC CCT GCT CTT TTT        462
Val Val Ala Arg Ile Ala Gln Leu Lys Asp Glu Tyr Pro Ala Leu Phe
     85                  90                  95

GCC TGG GAG ATC CAA CAC CAG CTT TGC ACT GAA GGG CTT TGT ACC CAG        510
Ala Trp Glu Ile Gln His Gln Leu Cys Thr Glu Gly Leu Cys Thr Gln
100                 105                 110                 115

GAC AAG GCT CCC AGT GTG TCC TCT ATC AAT CGA GTA CTT CGG GCA CTT        558
Asp Lys Ala Pro Ser Val Ser Ser Ile Asn Arg Val Leu Arg Ala Leu
                 120                 125                 130

CAG GAA GAC CAG AGC TTG CAC TGG ACT CAA CTC AGA TCA CCA GCT GTG        606
Gln Glu Asp Gln Ser Leu His Trp Thr Gln Leu Arg Ser Pro Ala Val
             135                 140                 145
```

```
TTG GCT CCA GTT CTT CCC AGT CCC CAC AGT AAC TGT GGG GCT CCC CGA      654
Leu Ala Pro Val Leu Pro Ser Pro His Ser Asn Cys Gly Ala Pro Arg
        150                 155                 160

GGC CCC CAC CCA GGA ACC AGC CAC AGG AAT CGG GCT ATC TTC TCC CCG      702
Gly Pro His Pro Gly Thr Ser His Arg Asn Arg Ala Ile Phe Ser Pro
165                 170                 175

GGA CAA GCC GAG GCA CTG GAG AAA GAG TTT CAG CGT GGG CAG TAT CCA      750
Gly Gln Ala Glu Ala Leu Glu Lys Glu Phe Gln Arg Gly Gln Tyr Pro
180                 185                 190                 195

GAT TCA GTG GCC CGT GGG AAG CTG GCT GCT GCC ACC TCT CTG CCT GAA      798
Asp Ser Val Ala Arg Gly Lys Leu Ala Ala Ala Thr Ser Leu Pro Glu
            200                 205                 210

GAC ACG GTG AGG GTT TGG TTT TCT AAC AGA AGA GCC AAA TGG CGC AGG      846
Asp Thr Val Arg Val Trp Phe Ser Asn Arg Arg Ala Lys Trp Arg Arg
                215                 220                 225

CAA GAG AAG CTG AAA TGG GAA GCA CAG CTG CCA GGT GCT TCC CAG GAC      894
Gln Glu Lys Leu Lys Trp Glu Ala Gln Leu Pro Gly Ala Ser Gln Asp
                    230                 235                 240

CTG ACG ATA CCA AAA AAT TCT CCA GGG ATC ATC TCT GCA CAG CAG TCC      942
Leu Thr Ile Pro Lys Asn Ser Pro Gly Ile Ile Ser Ala Gln Gln Ser
        245                 250                 255

CCC GGC AGT GTA CCC TCA GCT GCC TTG CCT GTG CTG GAA CCA TTG AGT      990
Pro Gly Ser Val Pro Ser Ala Ala Leu Pro Val Leu Glu Pro Leu Ser
260                 265                 270                 275

CCT TCC TTC TGT CAG CTA TGC TGT GGG ACA GCA CCA GGC AGA TGT TCC     1038
Pro Ser Phe Cys Gln Leu Cys Cys Gly Thr Ala Pro Gly Arg Cys Ser
                280                 285                 290

AGT GAC ACC TCA TCC CAG GCC TAT CTC CAA CCC TAC TGG GAC TGC AA      1086
Ser Asp Thr Ser Ser Gln Ala Tyr Leu Gln Pro Tyr Trp Asp Cys Gln
                    295                 300                 305

TCC CTC CTT CCT GTG GCT TCC TCA TAT GTG GAA TTT GCC TGC CCT         1134
Ser Leu Leu Pro Val Ala Ser Ser Tyr Val Glu Phe Ala Cys Pro
        310                 315                 320

GCC TCA CCA CCC ATC CTG TGC ATC ATC TGATTGGAGG CCCAGGACAA           1181
Ala Ser Pro Pro Ile Leu Cys Ile Ile
        325                 330

GTGCCATCAT CCCATTGCTC AAACTGGCCA TAAGACACCT CTATTTGACA GTAATAAAAA   1241

CCTTTTCTTA GATGTTAAAA AAAAAAAAGG GGGG                               1275

(2) INFORMATION FOR SEQ ID NO: 2:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO: 2:

Met Gln Gln Asp Gly Leu Ser Ser Val Asn Gln Leu Gly Gly Leu Phe
1               5                   10                  15

Val Asn Gly Arg Pro Leu Pro Leu Asp Thr Arg Gln Gln Ile Val Gln
            20                  25                  30

Leu Ala Ile Arg Gly Met Arg Pro Cys Asp Ile Ser Arg Ser Leu Lys
        35                  40                  45

Val Ser Asn Gly Cys Val Ser Lys Ile Leu Gly Arg Tyr Tyr Arg Thr
    50                  55                  60

Gly Val Leu Glu Pro Lys Cys Ile Gly Gly Ser Lys Pro Arg Leu Ala
65                  70                  75                  80
```

```
Thr Pro Ala Val Val Ala Arg Ile Ala Gln Leu Lys Asp Glu Tyr Pro
                85                  90                  95

Ala Leu Phe Ala Trp Glu Ile Gln His Gln Leu Cys Thr Glu Gly Leu
            100                 105                 110

Cys Thr Gln Asp Lys Ala Pro Ser Val Ser Ser Ile Asn Arg Val Leu
        115                 120                 125

Arg Ala Leu Gln Glu Asp Gln Ser Leu His Trp Thr Gln Leu Arg Ser
    130                 135                 140

Pro Ala Val Leu Ala Pro Val Leu Pro Ser Pro His Ser Asn Cys Gly
145                 150                 155                 160

Ala Pro Arg Gly Pro His Pro Gly Thr Ser His Arg Asn Arg Ala Ile
                165                 170                 175

Phe Ser Pro Gly Gln Ala Glu Ala Leu Glu Lys Glu Phe Gln Arg Gly
            180                 185                 190

Gln Tyr Pro Asp Ser Val Ala Arg Gly Lys Leu Ala Ala Ala Thr Ser
        195                 200                 205

Leu Pro Glu Asp Thr Val Arg Val Trp Phe Ser Asn Arg Arg Ala Lys
    210                 215                 220

Trp Arg Arg Gln Glu Lys Leu Lys Trp Glu Ala Gln Leu Pro Gly Ala
225                 230                 235                 240

Ser Gln Asp Leu Thr Ile Pro Lys Asn Ser Pro Gly Ile Ile Ser Ala
                245                 250                 255

Gln Gln Ser Pro Gly Ser Val Pro Ser Ala Ala Leu Pro Val Leu Glu
            260                 265                 270

Pro Leu Ser Pro Ser Phe Cys Gln Leu Cys Cys Gly Thr Ala Pro Gly
        275                 280                 285

Arg Cys Ser Ser Asp Thr Ser Ser Gln Ala Tyr Leu Gln Pro Tyr Trp
    290                 295                 300

Asp Cys Gln Ser Leu Leu Pro Val Ala Ser Ser Ser Tyr Val Glu Phe
305                 310                 315                 320

Ala Cys Pro Ala Ser Pro Pro Ile Leu Cys Ile Ile
                325                 330

(2) INFORMATION FOR SEQ ID NO: 3:

(i) SEQUENCE CHARACTERISTICS:
        (A) LENGTH: 2481 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(ix) FEATURE:
        (A) NAME/KEY: CDS
        (B) LOCATION:163..1470

(xi) SEQUENCE DESCRIPTION: SEQ ID NO: 3:

ACAACGACGA AAGAGAGGAT GCCTCTTAAA GGCAGAAGAC TTTAACCAAG GGCGGTGAGC      60

AGATGTGTGA GATCTTCTAT TCTAGAAGTG GACGTATATC CCAGTTCTCA GAGCCCCGTA    120

TTCGAGCCCC GTGGGATCCG GAGGCTGCCA ACCAGCTCCA GC ATG CAG AAC AGT      174
                                                Met Gln Asn Ser
                                                  1

CAC AGC GGA GTG AAT CAG CTT GGT GGT GTC TTT GTC AAC GGG CGG CCA      222
His Ser Gly Val Asn Gln Leu Gly Gly Val Phe Val Asn Gly Arg Pro
  5                  10                  15                  20

CTG CCG GAC TCC ACC CGG CAG AAG ATC GTA GAG CTA GCT CAC AGC GGG      270
```

-continued

```
Leu Pro Asp Ser Thr Arg Gln Lys Ile Val Glu Leu Ala His Ser Gly
             25                  30                  35

GCC CGG CCG TGC GAC ATT TCC CGA ATT CTG CAG ACC CAT GCA GAT GCA      318
Ala Arg Pro Cys Asp Ile Ser Arg Ile Leu Gln Thr His Ala Asp Ala
         40                  45                  50

AAA GTC CAG GTG CTG GAC AAT GAA AAC GTA TCC AAC GGT TGT GTG AGT      366
Lys Val Gln Val Leu Asp Asn Glu Asn Val Ser Asn Gly Cys Val Ser
             55                  60                  65

AAA ATT CTG GGC AGG TAT TAC GAG ACT GGC TCC ATC AGA CCC AGG GCA      414
Lys Ile Leu Gly Arg Tyr Tyr Glu Thr Gly Ser Ile Arg Pro Arg Ala
     70                  75                  80

ATC GGA GGG AGT AAG CCA AGA GTG GCG ACT CCA GAA GTT GTA AGC AAA      462
Ile Gly Gly Ser Lys Pro Arg Val Ala Thr Pro Glu Val Val Ser Lys
 85                  90                  95                 100

ATA GCC CAG TAT AAA CGG GAG TGC CCT TCC ATC TTT GCT TGG GAA ATC      510
Ile Ala Gln Tyr Lys Arg Glu Cys Pro Ser Ile Phe Ala Trp Glu Ile
                105                 110                 115

CGA GAC AGA TTA TTA TCC GAG GGG GTC TGT ACC AAC GAT AAC ATA CCC      558
Arg Asp Arg Leu Leu Ser Glu Gly Val Cys Thr Asn Asp Asn Ile Pro
                120                 125                 130

AGT GTG TCA TCA ATA AAC AGA GTT CTT CGC AAC CTG GCT AGC GAA AAG      606
Ser Val Ser Ser Ile Asn Arg Val Leu Arg Asn Leu Ala Ser Glu Lys
            135                 140                 145

CAA CAG ATG GGC GCA GAC GGC ATG TAT GAT AAA CTA AGG ATG TTG AAC      654
Gln Gln Met Gly Ala Asp Gly Met Tyr Asp Lys Leu Arg Met Leu Asn
    150                 155                 160

GGG CAG ACC GGA AGC TGG GGC ACA CGC CCT GGT TGG TAT CCC GGG ACT      702
Gly Gln Thr Gly Ser Trp Gly Thr Arg Pro Gly Trp Tyr Pro Gly Thr
165                 170                 175                 180

TCA GTA CCA GGG CAA CCC ACG CAA GAT GGC TGC CAG CAA CAG GAA GGA      750
Ser Val Pro Gly Gln Pro Thr Gln Asp Gly Cys Gln Gln Gln Glu Gly
                185                 190                 195

GGG GGA GAG AAC ACC AAC TCC ATC AGT TCT AAC GGA GAA GAC TCG GAT      798
Gly Gly Glu Asn Thr Asn Ser Ile Ser Ser Asn Gly Glu Asp Ser Asp
                200                 205                 210

GAA GCT CAG ATG CGA CTT CAG CTG AAG CGG AAG CTG CAA AGA AAT AGA      846
Glu Ala Gln Met Arg Leu Gln Leu Lys Arg Lys Leu Gln Arg Asn Arg
            215                 220                 225

ACA TCT TTT ACC CAA GAG CAG ATT GAG GCT CTG GAG AAA GAG TTT GAG      894
Thr Ser Phe Thr Gln Glu Gln Ile Glu Ala Leu Glu Lys Glu Phe Glu
    230                 235                 240

AGG ACC CAT TAT CCA GAT GTG TTT GCC CGG GAA AGA CTA GCA GCC AAA      942
Arg Thr His Tyr Pro Asp Val Phe Ala Arg Glu Arg Leu Ala Ala Lys
245                 250                 255                 260

ATA GAT CTA CCT GAA GCA AGA ATA CAG GTA TGG TTT TCT AAT CGA AGG      990
Ile Asp Leu Pro Glu Ala Arg Ile Gln Val Trp Phe Ser Asn Arg Arg
                265                 270                 275

GCC AAA TGG AGA AGA GAA GAG AAA CTG AGG AAC CAG AGA AGA CAG GCC     1038
Ala Lys Trp Arg Arg Glu Glu Lys Leu Arg Asn Gln Arg Arg Gln Ala
            280                 285                 290

AGC AAC ACT CCT AGT CAC ATT CCT ATC AGC AGC AGC TTC AGT ACC AGT     1086
Ser Asn Thr Pro Ser His Ile Pro Ile Ser Ser Ser Phe Ser Thr Ser
            295                 300                 305

GTC TAC CAG CCA ATC CCA CAG CCC ACC ACA CCT GTC TCC TCC TTC ACA     1134
Val Tyr Gln Pro Ile Pro Gln Pro Thr Thr Pro Val Ser Ser Phe Thr
    310                 315                 320

TCA GGT TCC ATG TTG GGC CGA ACA GAC ACC GCC CTC ACC AAC ACG TAC     1182
Ser Gly Ser Met Leu Gly Arg Thr Asp Thr Ala Leu Thr Asn Thr Tyr
325                 330                 335                 340
```

```
AGT GCT TTG CCA CCC ATG CCC AGC TTC ACC ATG GCA AAC AAC CTG CCT      1230
Ser Ala Leu Pro Pro Met Pro Ser Phe Thr Met Ala Asn Asn Leu Pro
            345                 350                 355

ATG CAA CCC CCA GTC CCC AGT CAG ACC TCC TCA TAC TCG TGC ATG CTG      1278
Met Gln Pro Pro Val Pro Ser Gln Thr Ser Ser Tyr Ser Cys Met Leu
            360                 365                 370

CCC ACC AGC CCG TCA GTG AAT GGG CGG AGT TAT GAT ACC TAC ACC CCT      1326
Pro Thr Ser Pro Ser Val Asn Gly Arg Ser Tyr Asp Thr Tyr Thr Pro
            375                 380                 385

CCG CAC ATG CAA ACA CAC ATG AAC AGT CAG CCC ATG GGC ACC TCG GGG      1374
Pro His Met Gln Thr His Met Asn Ser Gln Pro Met Gly Thr Ser Gly
            390                 395                 400

ACC ACT TCA ACA GGA CTC ATT TCA CCT GGA GTG TCA GTT CCC GTC CAA      1422
Thr Thr Ser Thr Gly Leu Ile Ser Pro Gly Val Ser Val Pro Val Gln
405                 410                 415                 420

GTT CCC GGG AGT GAA CCT GAC ATG TCT CAG TAC TGG CCT CGA TTA CAG      1470
Val Pro Gly Ser Glu Pro Asp Met Ser Gln Tyr Trp Pro Arg Leu Gln
                425                 430                 435

TAAAGAGAGA AGGAGAGAGC ATGTGATCGA GAGAGGAAAT TGTGTTCACT CTGCCAATGA    1530

CTATGTGGAC ACAGCAGTTG GGTATTCAGG AAAGAAAGAG AAATGGCGGT TAGAAGCACT    1590

TCACTTTGTA ACTGTCCTGA ACTGGAGCCC GGGAATGGAC TAGAACCAAG GACCTTGCGT    1650

ACAGAAGGCA CGGTATCAGT TGGAACAAAT CTTCATTTTG GTATCCAAAC TTTTATTCAT    1710

TTTGGTGTAT TATTTGTAAA TGGGCATTGG TATGTTATAA TGAAGAAAAG AACAACACAG    1770

GCTGTTGGAT CGCGGATCTG TGTTGCTCAT GTGGTTGTTT AAAGGAAACC ATGATCGACA    1830

AGATTTGCCA TGGATTTAAG AGTTTTATCA AGATATATCA AATACTTCTC CCCATCTGTT    1890

CATAGTTTAT GGACTGATGT TCCAAGTTTG TATCATTCCT TTGCATATAA TTGAACCTGG    1950

GACAACACAC ACTAGATATA TGTAAAAACT ATCTGTTGGT TTTCCAAAGG TTGTTAACAG    2010

ATGAAGTTTA TGTGCAAAAA AGGGTAAGAT ATGAATTCAA GGAGAAGTTG ATAGCTAAAA    2070

GGTAGAGTGT GTCTTCGATA TAATACAATT TGTTTTATGT CAAAATGTAA GTATTTGTCT    2130

TCCCTAGAAA TCCTCAGAAT GATTTCTATA ATAAAGTTAA TTTCATTTAT ATTTGACAAG    2190

AATACTCTAT AGATGTTTTA TACACATTTT CATGCAATCA TTTGTTTCTT TCTTGGCCAG    2250

CAAAAGTTAA TTGTTCTTAG ATATAGCTGT ATTACTGTTC ACAGTCCAAT CATTTTGTGC    2310

ATCTAGAATT CATTCCTAAT CAATTAAAAG TGCTTGCAAG AGTTTTAAAC CTAAGTGTTT    2370

TGCAGTTGTT CACAAATACA TATCAAAATT AACCATTGTT GATTGTAAAA AAAAAACCAT    2430

GCCAAAGCCT TTGTATTTTC TTTATTACCC TTGACCGTAA GACATGAATT C             2481

(2) INFORMATION FOR SEQ ID NO: 4:

(i) SEQUENCE CHARACTERISTICS:
        (A) LENGTH: 436 amino acids
        (B) TYPE: amino acid
        (D) TOPOLOGY: linear (ii) MOLECULE TYPE: protein (xi) SEQUENCE DESCRIPTION: SEQ ID NO: 4:

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45
```

-continued

```
His Ala Asp Ala Lys Val Gln Val Leu Asp Asn Glu Asn Val Ser Asn
     50                  55                  60
Gly Cys Val Ser Lys Ile Leu Gly Arg Tyr Tyr Glu Thr Gly Ser Ile
 65                  70                  75                  80
Arg Pro Arg Ala Ile Gly Gly Ser Lys Pro Arg Val Ala Thr Pro Glu
                     85                  90                  95
Val Val Ser Lys Ile Ala Gln Tyr Lys Arg Glu Cys Pro Ser Ile Phe
                100                 105                 110
Ala Trp Glu Ile Arg Asp Arg Leu Leu Ser Glu Gly Val Cys Thr Asn
            115                 120                 125
Asp Asn Ile Pro Ser Val Ser Ser Ile Asn Arg Val Leu Arg Asn Leu
        130                 135                 140
Ala Ser Glu Lys Gln Gln Met Gly Ala Asp Gly Met Tyr Asp Lys Leu
145                 150                 155                 160
Arg Met Leu Asn Gly Gln Thr Gly Ser Trp Gly Thr Arg Pro Gly Trp
                165                 170                 175
Tyr Pro Gly Thr Ser Val Pro Gly Gln Pro Thr Gln Asp Gly Cys Gln
                180                 185                 190
Gln Gln Glu Gly Gly Gly Glu Asn Thr Asn Ser Ile Ser Ser Asn Gly
            195                 200                 205
Glu Asp Ser Asp Glu Ala Gln Met Arg Leu Gln Leu Lys Arg Lys Leu
        210                 215                 220
Gln Arg Asn Arg Thr Ser Phe Thr Gln Glu Gln Ile Glu Ala Leu Glu
225                 230                 235                 240
Lys Glu Phe Glu Arg Thr His Tyr Pro Asp Val Phe Ala Arg Glu Arg
                245                 250                 255
Leu Ala Ala Lys Ile Asp Leu Pro Glu Ala Arg Ile Gln Val Trp Phe
                260                 265                 270
Ser Asn Arg Arg Ala Lys Trp Arg Arg Glu Glu Lys Leu Arg Asn Gln
            275                 280                 285
Arg Arg Gln Ala Ser Asn Thr Pro Ser His Ile Pro Ile Ser Ser Ser
        290                 295                 300
Phe Ser Thr Ser Val Tyr Gln Pro Ile Pro Gln Pro Thr Thr Pro Val
305                 310                 315                 320
Ser Ser Phe Thr Ser Gly Ser Met Leu Gly Arg Thr Asp Thr Ala Leu
                325                 330                 335
Thr Asn Thr Tyr Ser Ala Leu Pro Pro Met Pro Ser Phe Thr Met Ala
                340                 345                 350
Asn Asn Leu Pro Met Gln Pro Pro Val Pro Ser Gln Thr Ser Ser Tyr
            355                 360                 365
Ser Cys Met Leu Pro Thr Ser Pro Ser Val Asn Gly Arg Ser Tyr Asp
        370                 375                 380
Thr Tyr Thr Pro Pro His Met Gln Thr His Met Asn Ser Gln Pro Met
385                 390                 395                 400
Gly Thr Ser Gly Thr Thr Ser Thr Gly Leu Ile Ser Pro Gly Val Ser
                405                 410                 415
Val Pro Val Gln Val Pro Gly Ser Glu Pro Asp Met Ser Gln Tyr Trp
                420                 425                 430
Pro Arg Leu Gln
            435
```

(2) INFORMATION FOR SEQ ID NO: 5:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 5:

AGCAATAAGA GGGATGCGAC C                                           21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 6:

AGCTGTGCTT CCCATTTCAG C                                           21

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 7:

GCGAATTCCC TGAAGTGCCC GAAGTACTCG ATT                              33

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 8:

GGCTCCGTGA AATGTCACAG                                             20

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 9:

CGTAGTACTG TCGACTAGCA GGGNNGGGNN GGGNNG                           36

(2) INFORMATION FOR SEQ ID NO: 10:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 10:

CGTAGTACTG TCGACTAGCA                                                  20

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 11:

AACTGGAAGA ATTCGCGGCC GCAGGAA                                          27

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 12:

CAGGAAGACC AGAGCTTGCA CTGG                                             24

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 13:

GCGGATCCCA CAGGAATCGG GCTATCTTC                                        29

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 14:

GCGCAGGCAA GAGAAGCTGA                                                  20

(2) INFORMATION FOR SEQ ID NO: 15:
```

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "oligonucleotide"

(xi) SEQUENCE DESCRIPTION: SEQ ID NO: 15:

CTTCCAGAAG GAGCTCTC                                                18

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION:    /desc = "oligonucleotide"

(xi) SEQUENCE DESCRIPTION: SEQ ID NO: 16:

TGGGATGATG GCACTTGTC                                               19
```

What is claimed is:

1. A method for determining risk of developing juvenile diabetes based upon absence of Pax4 mRNA or protein in a mammal comprising:
   (a) determining the level or status of Pax4 mRNA in β-cells of said mammal; and/or
   (b) determining the level or status of Pax4 protein in β-cells of said mammal; and
   (c) comparing said level or status or Pax4 mRNA and/or Pax4 protein with the corresponding level in normal β-cells;

wherein the term "level" denotes the amount of mRNA or protein produced; and, the term "status" includes that the Pax4 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein, and from the comparing determining an absence of Pax4 mRNA or protein and thus risk of developing juvenile diabetes.

2. In a method for treating juvenile diabetes in a mammal comprising administering a medicament or treatment for a deficiency or failure of insulin production wherein the improvement comprises:
   (I) determining risk of developing juvenile diabetes based upon absence of Pax4 mRNA or protein in a mammal by a method comprising:
       (a) determining the level or status of Pax4 mRNA in β-cells of said mammal; and/or
       (b) determining the level or status of Pax4 protein in β-cells of said mammal; and
       (c) comparing said level or status of Pax4 mRNA and/or Pax4 protein with the corresponding level in normal β-cells;
   wherein the term "level" denotes the amount of mRNA or protein produced; and, the term "status" includes that the Pax4 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein, and from the comparing determining an absence of Pax4 mRNA or protein and thus risk of developing juvenile diabetes prior to administering the medicament or treatment if a risk of developing juvenile diabetes is indicated as a result of step (I), to thereby treat juvenile diabetes.

3. A method for testing a medicament for or a gene therapy approach to juvenile diabetes based on absence of Pax4 mRNA or protein comprising:
   (a') administering the medicament or the gene therapy;
   (a) determining the level or status of Pax4 mRNA in pancreatic cells of said mammal; and/or
   (b) determining the level or status of Pax4 protein in pancreatic cells of said mammal; and
   (c) comparing said level or status of Pax4 mRNA and/or Pax4 protein with the corresponding level in normal pancreatic cells;

wherein the term "level" denotes the amount of mRNA or protein produced; and, the term "status" includes that the Pax4 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein, and from the comparing determining an absence of Pax4 mRNA or protein and thus efficacy of the medicament or the gene therapy.

4. The method according to claim 1 further comprising
   (d) determining the level or status of Pax6 mRNA in pancreatic cells of said mammal; and/or
   (e) determining the level or status of Pax6 protein in pancreatic cells of said mammal; and
   (f) comparing said level or status of Pax6 mRNA and/or Pax6 protein with the corresponding level in normal pancreatic cells;

wherein the term "level" denotes the amount of mRNA or protein produced; and, the term "status" includes that the Pax6 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein, and from the comparing determining an absence of Pax6 mRNA or protein and thus risk of developing juvenile diabetes.

5. The method of claim 1 wherein said mammal is
   (i) an embryo;
   (ii) a newborn; or
   (iii) an adult.

6. The method according to claim 1 wherein said mammal is a mouse.

7. The method according to claim 1 wherein said mammal is a human.

8. The method according to claim 4, wherein steps (a) and/or (b) and optionally (d) and/or (e) are carried out in vivo.

9. The method according to claims 4, wherein steps (a) and/or (b) and optionally (d) and/or (e) are carried out in vitro.

10. The method according to claim 4 wherein said determination in step (a) and optionally in step (d) is effected by employing
    (i) a nucleic acid sequence corresponding to at least a part of the Pax4 gene encoding at least part of the Pax4 protein and optionally a second nucleic acid sequence corresponding to at least a part of the Pax6 gene encoding at least part of the Pax6 protein;
    (ii) a nucleic acid sequence complementary to the nucleic acid sequence(s) of (i); or
    (iii) a primer or a primer pair hybridizing to the nucleic acid sequence(s) of (i) or (ii).

11. The method according to claim 4, wherein said determination in step (b) and optionally of step (e) is effected by employing an antibody or a fragment thereof that specifically binds to the Pax4 protein and optionally by employing a second antibody or a fragment thereof which specifically binds to the Pax6 protein.

12. The method according to claim 2 comprising
    (d) determining the level or status of Pax6 mRNA in pancreatic cells of said mammal; and/or
    (e) determining the level or status of Pax6 protein in pancreatic cells of said mammal; and
    (f) comparing said level or status of Pax6 mRNA and/or Pax6 protein with the corresponding level in normal pancreatic cells;
wherein the term "level" denotes the amount of mRNA or protein produced; and, the term "status" includes that the Pax6 gene, mRNA, protein or a transcription control element, including a promoter/enhancer sequence, may bear a mutation, deletion or any other modifications which would affect the overall activity of the gene when compared to the wild-type normal gene product, including post-translational modifications of the protein, and from the comparing determining an absence of Pax6 mRNA or protein and thus risk of developing juvenile diabetes.

13. The method of claim 2 wherein said mammal is
    (i) an embryo;
    (ii) a newborn; or
    (iii) an adult.

14. The method according to claim 2 wherein said mammal is a mouse.

15. The method according to claim 2 wherein said mammal is a human.

16. The method according to claim 12, wherein steps (a) and/or (b) and optionally (d) and/or (e) are carried out in vivo.

17. The method according to claims 12, wherein steps (a) and/or (b) and optionally (d) and/or (e) are carried out in vitro.

18. The method according to claim 12 wherein said determination in step (a) and optionally in step (d) is effected by employing
    (i) a nucleic acid sequence corresponding to at least a part of the Pax4 gene encoding at least part of the Pax4 protein and optionally a second nucleic acid sequence corresponding to at least a part of the Pax6 gene encoding at least part of the Pax6 protein;
    (ii) a nucleic acid sequence complementary to the nucleic acid sequence(s) of (i); or
    (iii) a primer or a primer pair hybridizing to the nucleic acid sequence(s) of (i) or (ii).

19. The method according to claim 12, wherein said determination in step (b) and optionally of step (e) is effected by employing an antibody or a fragment thereof that specifically binds to the Pax4 protein and optionally by employing a second antibody or a fragment thereof which specifically binds to the Pax6 protein.

20. The method according to claim 3 further comprising
    (d) determining the level or status of Pax6 mRNA in pancreatic cells of said mammal; and/or
    (e) determining the level or status of Pax6 protein in pancreatic cells of said mammal; and
    (f) comparing said level or status of Pax6 mRNA and/or Pax6 protein with the corresponding level in normal pancreatic cells; wherein the term "level" denotes the amount of mRNA or protein produced; and, the term "status" includes that the Pax6 gene, mRNA, protein or a transcription control element, including a promoter/ enhancer sequence, may bear a mutation, deletion or any other modifications which would affect the overall activity of the gene when compared to the wild-type normal gene product, including post-tanslational modifications of the protein, and from the comparing, determining an absence of Pax6 mRNA or protein and thus efficacy of the medicament or the gene therapy.

21. The method of claim 3 wherein said mammal is
    (i) an embryo;
    (ii) a newborn; or
    (iii) an adult.

22. The method according to claim 3 wherein said mammal is a mouse.

23. The method according to claim 3 wherein said mammal is a human.

24. The method according to claim 20, wherein steps (a) and/or (b) and optionally (d) and/or (e) are carried out in vivo.

25. The method according to claims 20, wherein steps (a) and/or (b) and optionally (d) and/or (e) are carried out in vitro.

26. The method according to claim 20 wherein said determination in step (a) and optionally in step (d) is effected by employing
    (i) a nucleic acid sequence corresponding to at least a part of the Pax4 gene encoding at least part of the Pax4 protein and optionally a second nucleic acid sequence corresponding to at least a part of the Pax6 gene encoding at least part of the Pax6 protein;

(ii) a nucleic acid sequence complementary to the nucleic acid sequence(s) of (i); or (iii) a primer or a primer pair hybridizing to the nucleic acid sequence(s) of (i) or (ii).

27. The method according to claim 20, wherein said determination in step (b) and optionally of step (e) is effected by employing an antibody or a fragment thereof that specifically binds to the Pax4 protein and optionally by employing a second antibody or a fragment thereof which specifically binds to the Pax6 protein.

28. The method according to claim 2 wherein the medicament or treatment comprises: a compound which lowers blood glucose levels.

29. The method according to claim 2 wherein the medicament or treatment comprises: a compound which increases cellular uptake of glucose and its conversion to glycogen.

30. The method of claim 2 wherein in the medicament or treatment comprises: insulin.

31. The method of claim 29, wherein the mammal is a human, rat or mouse.

32. The method of claim 28, wherein the mammal is a human, rat or mouse.

33. The method of claim 30, wherein the mammal is a human, rat or mouse.

34. The method according to claim 32, wherein said β-cells are from an embryo or a newborn mammal.

35. The method according to claim 2, wherein said β-cells are from an embryo or a newborn mammal.

36. The method according to claim 3, wherein said β-cells are from an embryo or a newborn mammal.

37. The method according to claim 3, wherein said medicament affects the expression level of the Pax4 gene and optionally also affects the expression of the Pax6 gene at the mRNA or the protein level.

38. The method according to claim 3, wherein said testing is in Pax4 knockout mice that are optionally also Pax6 knockout mice.

39. The method according to claim 3, further comprising introducing into pancreatic or pancreatic ductal epithelial cells a Pax4 gene which is expressed and optionally further comprising introducing into pancreatic or pancreatic ductal epithelial cells a Pax6 gene which is expressed.

40. A functional Pax4 protein.

41. A composition comprising the functional Pax4 protein of claim 40 and optionally a functional Pax6 protein.

* * * * *